United States Patent
Kristjansdottir et al.

(10) Patent No.: US 8,871,939 B2
(45) Date of Patent: Oct. 28, 2014

(54) METHOD FOR PREPARING 2-AMINOBENZAMIDE DERIVATIVES

(75) Inventors: Sigridur Soley Kristjansdottir, Wilmington, DE (US); Rafael Shapiro, Wilmington, DE (US); Matthew Richard Oberholzer, Wilmington, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 13/981,919

(22) PCT Filed: Jan. 27, 2012

(86) PCT No.: PCT/US2012/022899
§ 371 (c)(1),
(2), (4) Date: Jul. 26, 2013

(87) PCT Pub. No.: WO2012/103436
PCT Pub. Date: Aug. 2, 2012

(65) Prior Publication Data
US 2013/0310567 A1 Nov. 21, 2013

Related U.S. Application Data

(60) Provisional application No. 61/437,280, filed on Jan. 28, 2011.

(51) Int. Cl.
| C07C 231/10 | (2006.01) |
| C07D 231/14 | (2006.01) |
| C07D 401/04 | (2006.01) |

(52) U.S. Cl.
CPC ............ *C07C 231/10* (2013.01); *C07D 231/14* (2013.01); *C07D 401/04* (2013.01)
USPC .......................................... 546/163; 564/168

(58) Field of Classification Search
USPC ................................. 564/163, 168
See application file for complete search history.

(56) References Cited

FOREIGN PATENT DOCUMENTS

| JP | 2004/043474 A1 | 2/2004 |
| JP | 2004/43474 A1 | 2/2004 |
| WO | 2006/061332 A1 | 6/2006 |
| WO | 2006/062978 A1 | 6/2006 |

OTHER PUBLICATIONS

Martinelli, Joseph, et al., "Convenient Method for the Preparation of Weinreb Amides via Pd-Catalyzed Aminocarbonylation of Aryl Bromides at Atmospheric Pressure", Organic Letters, 2006, vol. 8, No. 21, 4843-4846.

Albeneze-Walker, Jennifer, et al., "Improved Carbonylation of Heterocyclic Chlorides and Electronically Challenging Aryl Bromides", Organic Letters, 2004, vol. 6, No. 13, 2097-2108.

Kumar, Kamal, et al., "Palladium-Catalyzed Carbonylation of Haloindoles: No Need for Protecting Groups", Organic Letters, 2004, vol. 6, No. 1, 7-10.

Mori, Miwako, et al., "One Pot Synthesis of Quinazoline Derivatives by Use of Palladium Catalyzed Carbonylation", Heterocycles, 1985, vol. 23, No. 11, 2803-2806.

(Continued)

*Primary Examiner* — Patricia L Morris
(74) *Attorney, Agent, or Firm* — Renee M. Lett

(57) ABSTRACT

A method for preparing a compound of Formula 1 comprising contacting a compound of Formulae 2 and 3 in the presence of a palladium source, a ligand, a base and carbon monoxide

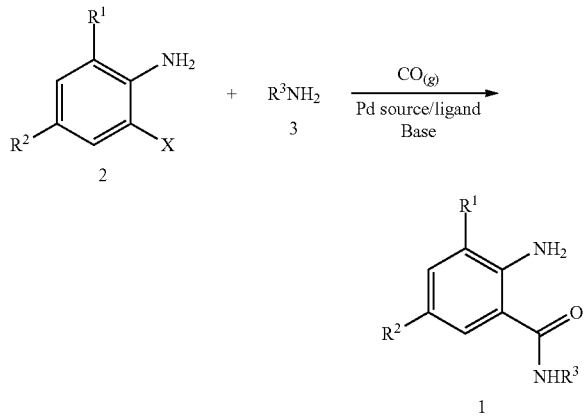

wherein $R^1$, $R^2$, X and $R^3$ are as defined in the disclosure.
A method for preparing a compound of Formula 5 wherein $R^1$, $R^2$, $R^3$, $R^4$, $R^5$, $R^6$ and Z are as defined in the disclosure, using a compound of Formula 1 characterized by preparing a compound of Formula 1 by the method disclosed above or using a compound of Formula 1 prepared by the method above.

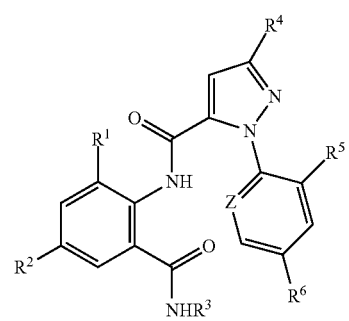

11 Claims, No Drawings

(56) References Cited

OTHER PUBLICATIONS

Fairlamb, Ian, et al., "Alkoxy- and Amidocarbonylation of Functionalised Aryl and Heteroaryl Halides Catalysed by a Bedford Palladacycle and DPPF: A Comparison with the Primary Pd(II) Precursors (PhCN)2PdCl2 and Pd(OAc)2", Dalton Trans., 2007, 859-865.

Acs, Peter, et al., "Palladium-Catalysed Carbonylation of 4-Substituted 2-Iodoaniline Derivatives: Carbonylative Cyclisation and Aminocarbonylation", Tetrahedron, 2006, vol. 62, 12051-12056.

Rama, Devi, et al., "A New Convergent Synthesis of WS-5995-B, An Anticoccidial Antibiotic From Streptomyces Auranticolor", 1994, Tetrahedron, vol. 50, No. 8, 2543-2550.

Vanlentine, Donald Jr., et al., "Practical, Catalytic Synthesis of Anthranilic Acids", 1981, J. Org. Chem. vol. 46, No. 22, 4614-4617.

METHOD FOR PREPARING 2-AMINOBENZAMIDE DERIVATIVES

FIELD OF THE INVENTION

This invention relates to a method for preparing 2-aminobenzamides and derivatives thereof.

BACKGROUND OF THE INVENTION

Preparation of certain 2-aminobenzamides and their utility as intermediates for preparing insecticidal anthranilic diamides is disclosed in PCT Patent Publication WO 06/062978. However, the need continues for new or improved methods suitable for rapidly and economically providing 2-aminobenzamides and their derivatives.

SUMMARY OF THE INVENTION

This invention is directed to a method for preparing a compound of Formula 1

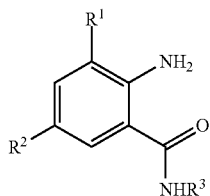

wherein
- $R^1$ is $C_1$-$C_4$ alkyl, $C_1$-$C_4$ haloalkyl, $C_1$-$C_4$ alkoxy or $C_1$-$C_6$ haloalkoxy;
- $R^2$ is F, Cl or cyano; and
- $R^3$ is H, $C_1$-$C_4$ alkyl, $C_3$-$C_6$ cycloalkyl, $C_4$-$C_7$ cycloalkylalkyl, $C_4$-$C_7$ alkylcycloalkyl or cyclopropylcyclopropyl;

comprising contacting a compound of Formula 2

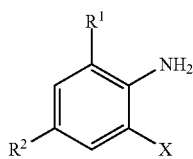

wherein
- $R^1$ is $C_1$-$C_4$ alkyl, $C_1$-$C_4$ haloalkyl, $C_1$-$C_4$ alkoxy or $C_1$-$C_6$ haloalkoxy;
- $R^2$ is F, Cl or cyano; and
- X is Br or I;

with a compound of Formula 3

wherein
- $R^3$ is H, $C_1$-$C_4$ alkyl, $C_3$-$C_6$ cycloalkyl, $C_4$-$C_7$ cycloalkylalkyl, $C_4$-$C_7$ alkylcycloalkyl or cyclopropylcyclopropyl;

in the presence of a palladium source, a ligand, a base and carbon monoxide.

This invention also relates to a method for preparing a compound of Formula 5

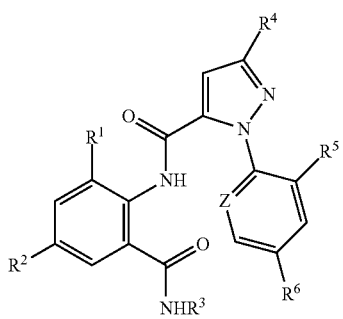

wherein
- $R^1$ is $C_1$-$C_4$ alkyl, $C_1$-$C_4$ haloalkyl, $C_1$-$C_4$ alkoxy or $C_1$-$C_6$ haloalkoxy;
- $R^2$ is F, Cl or cyano; and
- $R^3$ is H, $C_1$-$C_4$ alkyl, $C_3$-$C_6$ cycloalkyl, $C_4$-$C_7$ cycloalkylalkyl, $C_4$-$C_7$ alkylcycloalkyl or cyclopropylcyclopropyl;
- Z is $CR^7$ or N;
- $R^4$ is Cl, Br, $CF_3$, $OCHF_2$ or $OCH_2CF_3$;
- $R^5$ is F, Cl or Br;
- $R^6$ is H, F or Cl; and
- $R^7$ is H, F, Cl or Br using a compound of Formula 1, characterized by preparing a compound of Formula 1 from the compounds of Formulae 2 and 3 using the method disclosed above.

DETAILED DESCRIPTION OF THE INVENTION

As used herein, the terms "comprises," "comprising," "includes," "including," "has," "having," "contains", "containing," "characterized by" or any other variation thereof, are intended to cover a non-exclusive inclusion, subject to any limitation explicitly indicated. For example, a composition, mixture, process, method, article, or apparatus that comprises a list of elements is not necessarily limited to only those elements but may include other elements not expressly listed or inherent to such composition, mixture, process, method, article, or apparatus.

The transitional phrase "consisting of" excludes any element, step, or ingredient not specified. If in the claim, such phrase would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition, method or apparatus that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

Where applicants have defined an invention or a portion thereof with an open-ended term such as "comprising," it should be readily understood that (unless otherwise stated) the description should be interpreted to also describe such an invention using the terms "consisting essentially of" or "consisting of."

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

In the above recitations, the term "alkyl", used either alone or in compound words such as "haloalkyl" includes straight-chain or branched alkyl, such as, methyl, ethyl, n-propyl, i-propyl, or the different butyl isomers. The term "cycloalkyl" denotes a saturated carbocyclic ring consisting of 3 to 6 carbon atoms linked to one another by single bonds. Examples of "cycloalkyl" include cyclopropyl, cyclobutyl, cyclopentyl and cyclohexyl. The term "cycloalkylalkyl" denotes cycloalkyl substitution on an alkyl moiety. Examples of "cycloalkylalkyl" include cyclopropylmethyl, cyclopentylethyl and other cycloalkyl moieties bonded to straight-chain or branched alkyl groups. The term "alkylcycloalkyl" denotes alkyl substitution on a cycloalkyl moiety and includes, for example, 1-methylcyclopropyl, i-propylcyclobutyl, 3-methylcyclopentyl and 4-methylcyclohexyl.

The term "cyclopropylcyclopropyl," denotes cyclopropyl substitution on another cyclopropyl ring. Examples of "cyclopropylcyclopropyl," include 1,1'-bicyclopropyl-1-yl, 1,1'-bicyclopropyl-2-yl and the different cis- and trans-cyclopropylcyclopropyl isomers such as (1R,2S)-1,1'-bicyclopropyl-2-yl and (1R,2R)-1,1'-bicyclopropyl-2-yl.

"Alkoxy" includes, for example, methoxy, ethoxy, n-propyloxy, isopropyloxy and the different butoxy isomers. The term "halogen", either alone or in compound words such as "haloalkyl" or "haloalkoxy", includes fluorine, chlorine, bromine or iodine. Furthermore, when used in compound words such as "haloalkyl", said alkyl may be partially or fully substituted with halogen atoms which may be the same or different. Examples of "haloalkyl" include $F_3C$, $ClCH_2$, $CF_3CH_2$ and $CF_3CCl_2$. Examples of "haloalkoxy" include $CF_3O-$, $CCl_3CH_2O-$, $HCF_2CH_2CH_2O-$ and $CF_3CH_2O-$. "Hydroxyalkyl" denotes an alkyl group substituted with one hydroxy group. Examples of "hydroxyalkyl" include $HOCH_2$, $HOCH_2CH_2$ and $CH_3CH(OH)CH_2$. "Dialkylaminoalkyl" denotes two independent straight-chain or branched alkyl moieties bonded to a nitrogen atom of an amino (straight-chain or branched)alkyl moiety. Examples of "dialkylaminoalkyl" include $(CH_3)_2NCH_2-$, $(CH_3)_2CH(CH_3)NCH_2-$ and $(CH_3)_2NCH(CH_3)-$.

The total number of carbon atoms in a substituent group is indicated by the "$C_i$-$C_j$" prefix where i and j are numbers from 1 to 14. For example, $C_1$-$C_4$ alkoxy designates $CH_3O-$ through $CH_3CH_2CH_2CH_2O-$; and $C_6$ dialkylaminoalkyl designates the various isomers of an alkyl group substituted with a dislkylamino group containing a total of six carbon atoms, examples including $(CH_3CH_2CH_2CH_2)(CH_3)NCH_2-$ and $(CH_3CH_2CH_2)(CH_3)NCH(CH_3)-$. The term "combining" when used to describe a chemical reaction describes the act of "contacting" the referenced chemicals with each other, or, alternatively "reacting" the chemicals with each other. As used herein, the term "ligand" refers to an organic molecule comprising at least one pair of electrons available for coordination with a metal atom (in this case a palladium atom). Ligands in general can be neutral or charged, and can be unidentate, bidentate or higher. In the present invention, ratios are generally recited as single numbers, which are relative to the number 1; for example, a ratio of 4 means 4:1. In the present invention the term "mole ratio" refers to the number of moles of the specified reagent relative to the other specified reagent. Alternatively, the ratio may be expressed as a "mole percentage" which express the mole ratio as a percentage (i.e. mole ratio/100).

Embodiments of the present invention include:

Embodiment A1

The method described in the Summary of the Invention for preparing a compound of Formula 1 comprising contacting a compound of Formula 2 with a compound of Formula 3 in the presence of a palladium source, a ligand, a base and carbon monoxide.

Embodiment A2

The method of Embodiment A1 wherein $R^1$ is $C_1$-$C_4$ alkyl.

Embodiment A3

The method of Embodiment A2 wherein $R^1$ is methyl or ethyl.

Embodiment A4

The method of Embodiment A3 wherein $R^1$ is methyl.

Embodiment A5

The method of any one of Embodiments A1 through A4 wherein $R^2$ is chloro or cyano.

Embodiment A6

The method Embodiment A5 wherein $R^2$ is chloro.

Embodiment A7

The method Embodiment A5 wherein $R^2$ is cyano.

Embodiment A8

The method of any one of Embodiments A1 through A7 wherein $R^3$ is H, methyl, isopropyl, cyclopropyl, cyclobutyl, cyclopropylmethyl, methylcyclopropyl or cyclopropylcyclopropyl.

Embodiment A9

The method of Embodiment A8 wherein $R^3$ is H, methyl, isopropyl, cyclopropyl, cyclopropylmethyl or cyclopropylcyclopropyl.

Embodiment A10

The method of Embodiment A9 wherein $R^3$ is H, methyl, isopropyl or cyclopropylcyclopropyl.

Embodiment A11

The method Embodiment A10 wherein $R^3$ is cyclopropylcyclopropyl.

Embodiment A12

The method of Embodiment A10 wherein $R^3$ is methyl or isopropyl.

Embodiment A13

The method of Embodiment A12 wherein $R^3$ is methyl.

Embodiment A14

The method of Embodiment A12 wherein $R^3$ is isopropyl.

Embodiment A15

The method of any one of Embodiments A1 through A14 wherein X is Br.

Embodiment A16

The method of any one of Embodiments A1 through A14 wherein X is I.

Embodiment A17

The method of any one of Embodiments A1 through A16 wherein the palladium source is a palladium(II) species or a palladium(0) species.

Embodiment A18

The method of Embodiment A17 wherein the palladium source is a palladium(II) species.

Embodiment A19

The method of Embodiment A18 wherein the palladium source is a palladium(II) species selected from palladium(II) acetate (i.e. Pd(OAc)$_2$), palladium(II) chloride (i.e. PdCl$_2$), bis(benzonitrile)palladium(II) chloride (i.e. Pd(PhCN)$_2$Cl$_2$) and palladium(II) acetylacetonate (i.e. Pd(acac)$_2$).

Embodiment A20

The method of Embodiment A19 wherein the palladium source is a palladium(II) species selected from palladium(II) acetate and palladium(II) chloride.

Embodiment A21

The method of Embodiment A20 wherein the palladium source is palladium(II) acetate.

Embodiment A22

The method of Embodiment A20 wherein the palladium source is palladium(II) chloride.

Embodiment A23

The method of Embodiment A17 wherein the palladium source is a palladium(0) species.

Embodiment A24

The method of Embodiment A23 wherein the palladium source is a palladium(0) species selected from tris(dibenzylideneacetone)dipalladium(0) and bis(dibenzylideneacetone)dipalladium(0).

Embodiment A25

The method of Embodiment A24 wherein the palladium source is a palladium(0) species and is tris(dibenzylideneacetone)dipalladium(0).

Embodiment A26

The method of any one of Embodiments A1 through A25 wherein the mole percentage of the palladium source relative to the compound of Formula 2 is at least about 0.1%.

Embodiment A27

The method of Embodiment A26 wherein the mole percentage of the palladium source relative to the compound of Formula 2 is at least about 0.2%.

Embodiment A28

The method of Embodiment A27 wherein the mole percentage of the palladium source relative to the compound of Formula 2 is at least about 0.4%.

Embodiment A29

The method of any one of Embodiments A26 through A27 wherein the mole percentage of the palladium source relative to the compound of Formula 2 is less than about 0.4%.

Embodiment A30

The method of any one of Embodiments A1 through A30 wherein the ligand is a monodentate phosphine ligand or a bidentate bisphosphine ligand.

Embodiment A31

The method of Embodiment A30 wherein the ligand is a bidentate bisphosphine ligand selected from 1,1'-bis(diphenylphosphino)ferrocene (i.e. dppf), 1,4-bis(diphenylphosphino)butane (i.e. dppb), 9,9-dimethyl-4,5-bis(diphenylphosphino)xanthene (i.e. XANTPHOS) and bis(2-diphenylphosphinophenyl)ether (i.e. DPEphos).

Embodiment A32

The method of Embodiment A31 wherein the ligand is a bidentate bisphosphine ligand selected from 1,1'-bis(diphenylphosphino)ferrocene and 1,4-bis(diphenylphosphino)butane.

Embodiment A33

The method of Embodiment A31 wherein the ligand is 1,4-bis(diphenylphosphino)butane.

Embodiment A34

The method of Embodiment A31 wherein the ligand is 1,1'-bis(diphenylphosphino)ferrocene.

Embodiment A35

The method of any one of Embodiments A1 through A34 wherein the ligand is a bidentate ligand and the mole ratio of bidentate ligand to palladium source is at least about 1.

Embodiment A36

The method of Embodiment A35 wherein the ligand is a bidentate ligand and the mole ratio of bidentate ligand to palladium source is at least about 1.5.

Embodiment A37

The method of Embodiment A36 wherein the ligand is a bidentate ligand and the mole ratio of bidentate ligand to palladium source is at least about 3.

Embodiment A38

The method of any one of Embodiments A35 through A37 wherein the ligand is a bidentate ligand and the mole ratio of bidentate ligand to palladium source is less than about 10.

Embodiment A39

The method of any one of Embodiments A1 through A38 wherein the base is an organic base or an inorganic base.

Embodiment A40

The method of Embodiment A39 wherein the base is an organic base selected from trimethylamine, triethylamine, tributylamine and N,N-dimethylisopropylamine.

Embodiment A41

The method of Embodiment A40 wherein the base is an organic base selected from triethylamine and tributylamine.

Embodiment A42

The method of Embodiment A41 wherein the base is triethylamine.

Embodiment A43

The method of A39 wherein the base comprises a compound of Formula 3 in sufficient amount to act as both a reagent and a base.

Embodiment A44

The method of Embodiment A39 or A43 wherein the base is an inorganic base comprising a compound of Formula 3; $R^3$ is H; and the base is in a mole ratio of at least about 2 relative to a compound of Formula 2 (i.e. the method of Embodiment A39 or A43 wherein the base is $NH_3$; and the base is in a mole ratio of at least about 2 relative to a compound of Formula 2.).

Embodiment A45

The method of Embodiment A39 or A43 wherein the base is an organic base comprising a compound of Formula 3 wherein $R^3$ is methyl, isopropyl, cyclopropyl, cyclopropylmethyl or cyclopropylcyclopropyl (i.e. the base is $NH_2CH_3$, $NH_2CH(CH_3)_2$, $NH_2(c\text{-}Pr)$ or $NH_2CH_2(c\text{-}Pr)$; and the base is in a mole ratio of at least about 2 relative to a compound of Formula 2.

Embodiment A46

The method of Embodiment A45 wherein the base is an organic base comprising a compound of Formula 3; $R^3$ is methyl or isopropyl; and the base is in a mole ratio of at least about 2 relative to a compound of Formula 2.

Embodiment A47

The method of Embodiment A46 wherein the base is an organic base comprising a compound of Formula 3; $R^3$ is methyl; and the base is in a mole ratio of at least about 2 relative to a compound of Formula 2.

Embodiment A48

The method of Embodiment A39 wherein the base is an inorganic base selected from sodium carbonate and sodium bicarbonate.

Embodiment A49

The method of Embodiment A48 wherein the base is sodium carbonate.

Embodiment A50

The method of Embodiment A49 wherein the base is sodium bicarbonate.

Embodiment A51

The method of any one of Embodiments A48 through A50 wherein the mole ratio of the base to a compound of Formula 2 is at least about 1.

Embodiment A52

The method of any one of Embodiments A1 through A51 wherein the mole ratio of the base to a compound of Formula 2 is at least about 2.

Embodiment A53

The method of any one of Embodiments A51 through A52 wherein the mole ratio of the base to a compound of Formula 2 is less than about 5.

Embodiment A54

The method of any one of Embodiments A1 through A53 wherein the contacting is performed in a suitable solvent.

Embodiment A55

The method of Embodiment A54 wherein the contacting is performed in a suitable solvent comprising one or more organic solvents selected from ethers, nitriles, aromatic hydrocarbons and alcohols.

Embodiment A56

The method of Embodiment A55 wherein the contacting is performed in a suitable solvent comprising one or more organic solvents selected from tetrahydrofuran, glyme, acetonitrile, xylenes, toluene, methanol, ethylene glycol and N,N-dimethylethanolamine.

Embodiment A57

The method of Embodiment A56 wherein the contacting is performed in a suitable solvent comprising ethylene glycol.

Embodiment A58

The method of Embodiment A56 wherein the contacting is performed in a suitable solvent comprising N,N-dimethylethanolamine (also know as 2-dimethylaminoethanol).

Embodiment A59

The method of Embodiment A56 wherein the contacting is performed in a suitable solvent comprising a mixture of ethylene glycol and N,N-dimethylethanolamine.

Embodiment A60

The method of any one of Embodiments A1 through A59 wherein the ratio of the volume of the suitable solvent to the weight of a compound of Formula 2 is at least about 1 mL/g

Embodiment A61

The method of Embodiment A60 wherein the ratio of the volume of the suitable solvent to the weight of a compound of Formula 2 is at least about 6 mL/g.

Embodiment A62

The method of Embodiment A61 wherein the ratio of the volume of the suitable solvent to the weight of a compound of Formula 2 is at least about 10 mL/g

Embodiment A63

The method of any one of Embodiments A60 or A61 wherein the ratio of the volume of the suitable solvent to the weight of a compound of Formula 2 is less than about 10 mL/g

Embodiment A64

The method of any one of Embodiments A1 through A63 wherein the contacting is performed at a pressure of at least about 20 psi (about 1.379e+005 newtons/square meter) of carbon monoxide.

Embodiment A65

The method of Embodiment A64 wherein the contacting is performed at a pressure of at least about 40 psi (about 2.758e+005 newtons/square meter) of carbon monoxide.

Embodiment A66

The method of Embodiment A65 wherein the contacting is performed at a pressure of at least about 75 psi (about 5.171e+005 newtons/square meter) of carbon monoxide.

Embodiment A67

The method of any one of Embodiments A64 through A66 wherein the contacting is performed at a pressure of less than about 100 psi (about 6.895e+005 newtons/square meter) of carbon monoxide.

Embodiment A68

The method of any one of Embodiments A1 through A67 wherein the contacting is performed at a temperature not greater than about 150° C.

Embodiment A69

The method of Embodiment A68 wherein the contacting is performed at a temperature not greater than about 120° C.

Embodiment A70

The method of Embodiment A69 wherein the contacting is performed at a temperature not greater than about 100° C.

Embodiment A71

The method of any one of Embodiments A68 through A70 wherein the contacting is performed at a temperature greater than 70° C.

Embodiment A72

The method of Embodiment A56 wherein the contacting is performed in a suitable solvent consisting of ethylene glycol and N,N-dimethylethanolamine.

Embodiment B1

A method for preparing a compound of Formula 1 in the Summary of the Invention comprising preparing a compound of Formula 4

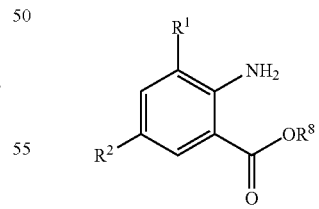

4 wherein
- $R^1$ is $C_1$-$C_4$ alkyl, $C_1$-$C_4$ haloalkyl, $C_1$-$C_4$ alkoxy or $C_1$-$C_6$ haloalkoxy;
- $R^2$ is F, Cl or cyano; and
- $R^8$ is $C_1$-$C_{14}$ alkyl, $C_2$-$C_{14}$ hydroxyalkyl, $C_3$-$C_{14}$ dialkylaminoalkyl, or $C_3$-$C_{14}$ halodialkylaminoalkyl by contacting a compound of Formula 2

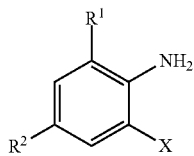

2 wherein
R$^1$ is C$_1$-C$_4$ alkyl, C$_1$-C$_4$ haloalkyl, C$_1$-C$_4$ alkoxy or C$_1$-C$_6$ haloalkoxy;
R$^2$ is F, Cl or cyano;
X is Br or I;
with a compound of Formula 6

R$^8$OH     6 in the presence of a palladium source, a ligand, a base and carbon monoxide; followed by aminating in the presence of a compound of Formula 3.

Embodiment B2

The method of Embodiment B1 wherein R$^8$ in the compound of Formula 4 is C$_1$-C$_{14}$ alkyl, C$_2$-C$_{14}$ hydroxyalkyl or C$_3$-C$_{14}$ dialkylaminoalkyl.

Embodiment B3

The method of Embodiment B1 wherein R$^8$ in the compound of Formula 4 is methyl, ethyl, isopropyl, hydroxyethyl, hydroxypropyl or dimethylaminoethyl.

Embodiment B4

The method of Embodiment B1 wherein R$^8$ in the compound of Formula 4 is methyl, ethyl, isopropyl, hydroxyethyl or dimethylaminoethyl.

Embodiment B5

The method of Embodiment B1 wherein R$^8$ in the compound of Formula 4 is hydroxyethyl or dimethylaminoethyl.

Embodiment B6

The method of Embodiment B1 wherein R$^8$ is in the compound of Formula 4 hydroxyethyl.

Embodiment B7

The method of Embodiment B1 wherein R$^8$ in the compound of Formula 4 is dimethylaminoethyl.

Embodiment B8

The method of any one of Embodiments B1 through B7 wherein R$^1$ is C$_1$-C$_4$ alkyl.

Embodiment B9

The method of Embodiment B8 wherein R$^1$ is methyl or ethyl.

Embodiment B10

The method of Embodiment B9 wherein R$^1$ is methyl.

Embodiment B11

The method of any one of Embodiments B1 through B10 wherein R$^2$ is chloro or cyano.

Embodiment B12

The method of Embodiment B11 wherein R$^2$ is chloro.

Embodiment B13

The method of Embodiment B11 wherein R$^2$ is cyano.

Embodiment B14

The method of Embodiment B1 wherein R$^8$ in the compound of Formula 6 is C$_1$-C$_{14}$ alkyl, C$_2$-C$_{14}$ hydroxyalkyl or C$_3$-C$_{14}$ dialkylaminoalkyl.

Embodiment B15

The method of Embodiment B14 wherein R$^8$ in the compound of Formula 6 is methyl, ethyl, isopropyl, hydroxyethyl, hydroxypropyl or dimethylaminoethyl.

Embodiment B16

The method of Embodiment B15 wherein R$^8$ in the compound of Formula 6 is methyl, ethyl, isopropyl, hydroxyethyl or dimethylaminoethyl.

Embodiment B17

The method of Embodiment B16 wherein R$^8$ in the compound of Formula 6 is hydroxyethyl or dimethylaminoethyl.

Embodiment B18

The method of Embodiment B17 wherein R$^8$ is in the compound of Formula 6 hydroxyethyl.

Embodiment B19

The method of Embodiment B17 wherein R$^8$ in the compound of Formula 6 is dimethylaminoethyl.

Embodiment B20

The method of any one of Embodiments B1 through B19 wherein X is Br.

Embodiment B21

The method of any one of Embodiments B1 through B19 wherein X is I.

Embodiment B22

The method of any one of Embodiments B1 through B21 wherein a compound of Formula 4 is isolated.

Embodiment B23

The method of any one of Embodiments B1 through B21 wherein a compound of Formula 4 is other than isolated (i.e. prepared in-situ).

Embodiment B24

The method of any one of Embodiments B1 through B23 wherein the palladium source is a palladium(II) species or a palladium(0) species.

Embodiment B25

The method of Embodiment B24 wherein the palladium source is a palladium(II) species.

Embodiment B26

The method of Embodiment B25 wherein the palladium source is a palladium(II) species selected from palladium(II) acetate (i.e. Pd(OAc)$_2$), palladium(II) chloride (i.e. PdCl$_2$), bis(benzonitrile)palladium(II) chloride (i.e. Pd(PhCN)$_2$Cl$_2$) and palladium(II) acetylacetonate (i.e. Pd(acac)$_2$).

Embodiment B27

The method of Embodiment B26 wherein the palladium source is a palladium(II) species selected from palladium(II) acetate and palladium(II) chloride.

Embodiment B28

The method of Embodiment B27 wherein the palladium source is palladium(II) acetate.

Embodiment B29

The method of Embodiment B27 wherein the palladium source is palladium(II) chloride.

Embodiment B30

The method of Embodiment B24 wherein the palladium source is a palladium(0) species.

Embodiment B31

The method of Embodiment B30 wherein the palladium source is a palladium(0) species selected from tris(dibenzylideneacetone)dipalladium(0) and bis(dibenzylidineacetone)dipalladium(0).

Embodiment B32

The method of Embodiment B31 wherein the palladium source is a palladium(0) species and is tris(dibenzylideneacetone)dipalladium(0).

Embodiment B33

The method of any one of Embodiments B1 through B32 wherein the mole percentage of the palladium source relative to a compound of Formula 2 is at least about 0.1%.

Embodiment B34

The method of Embodiment B33 wherein the mole percentage of the palladium source relative to a compound of Formula 2 is at least about 0.2%.

Embodiment B35

The method of Embodiment B34 wherein the mole percentage of the palladium source relative to a compound of Formula 2 is at least about 0.4%.

Embodiment B36

The method of any one of Embodiments B33 or B34 wherein the mole percentage of the palladium source relative to a compound of Formula 2 is less than about 0.4%.

Embodiment B37

The method of any one of Embodiments B1 through B36 wherein the ligand is a monodentate phosphine ligand or a bidentate bisphosphine ligand.

Embodiment B38

The method of Embodiment B37 wherein the ligand is a bidentate bisphosphine ligand selected from 1,1'-bis(diphenylphosphino)ferrocene (i.e. dppf), 1,4-bis(diphenylphosphino)butane (i.e. dppb), 9,9-dimethyl-4,5-bis(diphenylphosphino)xanthene (i.e. XANTPHOS) and bis(2-diphenylphosphinophenyl)ether (i.e. DPEphos).

Embodiment B39

The method of Embodiment B38 wherein the ligand is a bidentate bisphosphine ligand selected from 1,1'-bis(diphenylphosphino)ferrocene and 1,4-bis(diphenylphosphino)butane.

Embodiment B40

The method of Embodiment B39 wherein the ligand is 1,4-bis(diphenylphosphino)butane.

Embodiment B41

The method of Embodiment B39 wherein the ligand is 1,1'-bis(diphenylphosphino)ferrocene.

Embodiment B42

The method of any one of Embodiments B1 through B41 wherein the ligand is a bidentate ligand and the mole ratio of bidentate ligand to palladium source is at least about 1.

Embodiment B43

The method of Embodiment B42 wherein the ligand is a bidentate ligand and the mole ratio of bidentate ligand to palladium source is at least about 1.5.

Embodiment B44

The method of Embodiment B43 wherein the ligand is a bidentate ligand and the mole ratio of bidentate ligand to palladium source is at least about 3.

Embodiment B45

The method of any one of Embodiments B42 through B44 wherein the ligand is a bidentate ligand and the mole ratio of bidentate ligand to palladium source is less than about 10.

Embodiment B46

The method of any one of Embodiments B1 through B45 wherein the base is an organic base or an inorganic base.

Embodiment B47

The method of Embodiment B46 wherein the base is an organic base selected from trimethylamine, triethylamine, tributylamine and N,N-dimethylisopropylamine.

Embodiment B48

The method of Embodiment B47 wherein the base is an organic base selected from triethylamine and tributylamine.

Embodiment B49

The method of Embodiment B48 wherein the base is triethylamine.

Embodiment B50

The method of Embodiment B46 wherein the base is an inorganic base selected from sodium carbonate and sodium bicarbonate.

Embodiment B51

The method of Embodiment B50 wherein the base is sodium carbonate.

Embodiment B52

The method of any one of Embodiments B1 through B51 wherein the mole ratio of the base to a compound of Formula 2 is at least about 1.

Embodiment B53

The method Embodiment B52 wherein the mole ratio of the base to a compound of Formula 2 is at least about 2.

Embodiment B54

The method of any one of Embodiments B52 through B53 wherein the mole ratio of the base to a compound of Formula 2 is less than about 5.

Embodiment B55

The method Embodiments B1 through B54 wherein the contacting is performed in a suitable solvent.

Embodiment B56

The method of Embodiment B55 wherein the contacting is performed in a suitable solvent comprising one or more organic solvents selected from ethers, nitriles, aromatic hydrocarbons and alcohols.

Embodiment B57

The method of Embodiment B56 wherein the contacting is performed in a suitable solvent comprising one or more organic solvents selected from tetrahydrofuran, glyme, acetonitrile, xylenes, toluene, methanol, ethylene glycol and N,N-dimethylethanolamine (also know as 2-dimethylaminoethanol).

Embodiment B58

The method of Embodiment B57 wherein the contacting is performed in a suitable solvent comprising ethylene glycol.

Embodiment B59

The method of Embodiment B57 wherein the contacting is performed in a suitable solvent comprising a mixture of ethylene glycol and N,N-dimethylethanolamine.

Embodiment B60

The method of any one of Embodiments B1 through B59 wherein the ratio of the volume of the suitable solvent to the weight of a compound of Formula 2 is at least about 1 mL/g

Embodiment B61

The method of Embodiment B60 wherein the ratio of the volume of suitable solvent to the weight of a compound of Formula 2 is at least about 6 mL/g

Embodiment B62

The method of Embodiment B61 wherein the ratio of the volume of suitable solvent to the weight of a compound of Formula 2 is at least about 10 mL/g

Embodiment B63

The method of any one of Embodiments B60 through B61 wherein the ratio of the volume of the suitable solvent to the weight of a compound of Formula 2 is less than about 10 mL/g

Embodiment B64

The method of Embodiment B59 wherein the contacting is performed in a suitable solvent comprising ethylene glycol and N,N-dimethylethanolamine and the molar ratio of N,N-dimethylethanolamine is 3.5 relative to a compound of Formula 2.

Embodiment B65

The method of any one of Embodiments B1 through B64 wherein the contacting is performed at a pressure of at least about 20 psi (about 1.379e+005 newtons/square meter) of carbon monoxide.

Embodiment B66

The method of Embodiment B65 wherein the contacting is performed at a pressure of at least about 40 psi (about 2.758e+005 newtons/square meter) of carbon monoxide.

Embodiment B67

The method of Embodiment B66 wherein the contacting is performed at a pressure of at least about 75 psi (about 5.171e+005 newtons/square meter) of carbon monoxide.

Embodiment B68

The method of any one of Embodiments B65 through B67 wherein the contacting is performed at a pressure of less than about 100 psi (about 6.895e+005 newtons/square meter) of carbon monoxide.

Embodiment B69

The method of any one of Embodiments B1 through B68 wherein the contacting is performed at a temperature not greater than about 140° C.

Embodiment B70

The method of Embodiment B69 wherein the contacting is performed at a temperature not greater than about 130° C.

Embodiment B71

The method of Embodiment B70 wherein the contacting is performed at a temperature not greater than about 120° C.

Embodiment B72

The method of any one of Embodiments B69 through B71 wherein the contacting is performed at a temperature greater than 70° C.

Embodiment B73

The method of any one of Embodiments B69 through B71 wherein the contacting is performed at a temperature greater than 90° C.

Embodiment B74

The method of any one of Embodiments B1 through B73 wherein $R^3$ is H, methyl, isopropyl, cyclopropyl, cyclobutyl, cyclopropylmethyl, methylcyclopropyl or cyclopropylcyclopropyl.

Embodiment B75

The method of Embodiment B74 wherein $R^3$ is H, methyl, isopropyl, cyclopropyl, cyclopropylmethyl or cyclopropylcyclopropyl.

Embodiment B76

The method of Embodiment B75 wherein $R^3$ is H, methyl, isopropyl or cyclopropylcyclopropyl.

Embodiment B77

The method Embodiment B76 wherein $R^3$ is cyclopropylcyclopropyl.

Embodiment B78

The method of Embodiment B76 wherein $R^3$ is methyl or isopropyl.

Embodiment B79

The method of Embodiment B78 wherein $R^3$ is methyl.

Embodiment B80

The method of Embodiment B78 wherein $R^3$ is isopropyl.

Embodiment B81

The method of Embodiment B58 wherein the contacting is performed in a suitable solvent consisting of a mixture of ethylene glycol and N,N-dimethylethanolamine.

Embodiment B82

The method of Embodiment B59 wherein the contacting is performed in a suitable solvent comprising ethylene glycol and N,N-dimethylethanolamine and the molar ratio of N,N-dimethylethanolamine is from about 1 to about 14 relative to a compound of Formula 2.

Embodiment B83

The method of Embodiment B84 wherein the contacting is performed in a suitable solvent comprising ethylene glycol and N,N-dimethylethanolamine and the molar ratio of N,N-dimethylethanolamine is from about 1 to about 8 relative to a compound of Formula 2.

Embodiment B84

The method of Embodiment B83 wherein the contacting is performed in a suitable solvent comprising ethylene glycol and N,N-dimethylethanolamine and the molar ratio of N,N-dimethylethanolamine is from about 2 to about 4 relative to a compound of Formula 2.

Embodiment C1

The method of the Summary of the Invention for preparing a compound of Formula 5 using a compound of Formula 1 characterized by preparing a compound of Formula 1 using the method disclosed in any of Embodiments A1 through A72 or B1 through B84.

Embodiment C2

The method of Embodiment C1 wherein Z in the compound of Formula 5 is N.

Embodiment C3

The method of Embodiment C1 wherein Z in the compound of Formula 5 is $CR^7$.

Embodiment C4

The method of any one of Embodiments C1 or C3 wherein $R^7$ is H, Cl or Br.

Embodiment C5

The method of Embodiment C4 wherein $R^7$ is Cl.

Embodiment C6

The method of Embodiment C4 wherein $R^7$ is H.

Embodiment C7

The method of any one of Embodiments C1 through C6 wherein $R^1$ in the compound of Formula 5 is $C_1$-$C_4$ alkyl.

Embodiment C8

The method of Embodiment C7 wherein $R^1$ is methyl or ethyl.

Embodiment C9

The method of Embodiment C7 wherein $R^1$ is methyl.

Embodiment C10

The method of any one of Embodiments C1 through C9 wherein $R^2$ in the compound of Formula 5 is chloro or cyano.

Embodiment C11

The method Embodiment C10 wherein $R^2$ is chloro.

Embodiment C12

The method Embodiment C10 wherein $R^2$ is cyano.

Embodiment C13

The method of any one of Embodiments C1 through C12 wherein $R^3$ in the compound of Formula 5 is H, methyl, isopropyl, cyclopropyl, cyclobutyl, cyclopropylmethyl, methylcyclopropyl or cyclopropylcyclopropyl.

Embodiment C14

The method of Embodiment C13 wherein $R^3$ is H, methyl, isopropyl, cyclopropyl, cyclopropylmethyl or cyclopropylcyclopropyl.

Embodiment C15

The method of Embodiment C14 wherein $R^3$ is H, methyl, isopropyl or cyclopropylcyclopropyl.

Embodiment C16

The method Embodiment C15 wherein $R^3$ is cyclopropylcyclopropyl.

Embodiment C17

The method of Embodiment C15 wherein $R^3$ is methyl or isopropyl.

Embodiment C18

The method of Embodiment C17 wherein $R^3$ is methyl.

Embodiment C19

The method of Embodiment C17 wherein $R^3$ is isopropyl.

Embodiment C20

The method of any one of Embodiments C1 through C19 wherein $R^4$ in the compound of Formula 5 is Cl, Br, $CF_3$ or $OCHF_2$.

Embodiment C21

The method of Embodiment C20 wherein $R^4$ is Br or $CF_3$.

Embodiment C22

The method of Embodiment C21 wherein $R^4$ is $CF_3$.

Embodiment C23

The method of Embodiment C21 wherein $R^4$ is Br.

Embodiment C24

The method of any one of Embodiments C1 through C23 wherein $R^5$ in the compound of Formula 5 is Cl or Br.

Embodiment C25

The method of Embodiment C24 wherein $R^5$ is Br.

Embodiment C26

The method of Embodiment C24 wherein $R^5$ is Cl.

Embodiment C27

The method of any one of Embodiments C1 through C26 wherein $R^6$ in the compound of Formula 5 is H or Cl.

Embodiment C28

The method of Embodiment C27 wherein $R^6$ is H.

Any of the above Embodiments A1 through A72, B1 through B84 or C1 through C28 of this invention can be combined in any manner.

In the following Schemes the definitions of $R^1$, $R^2$, $R^3$, $R^4$, $R^5$, $R^6$, and $R^7$ in the compounds of Formulae 1 through 8 below are as defined above in the Summary of the Invention unless otherwise indicated. As shown in Scheme 1, this invention relates to a method for preparing a compound of Formula 1 using palladium catalyzed carbonylation followed by amination, the whole process surprisingly being accomplished without protection of the aniline functionality. In the present method an aniline of Formula 2 and an amine of Formula 3 are combined (i.e. contacted) in the presence of a palladium source, a ligand, a base and carbon monoxide to provide the corresponding aminobenzamides of Formula 1.

Scheme 1

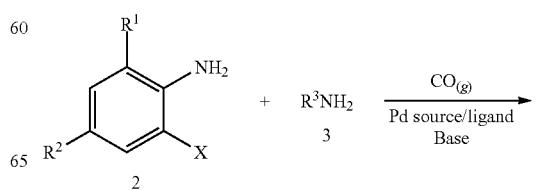

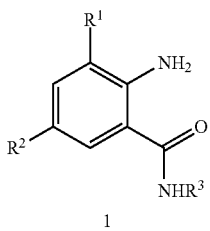

The palladium source can be either a Pd(0) or a Pd(II) species. The ligand of the present invention can be a bidentate phosphine such as the compound of Formula 7 as shown below in FIG. 1.

Figure 1

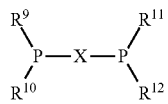

In a compound of Formula 7, X is a substituted or unsubstituted bridging group selected such that the bite angle of the ligand is between 91 and 112 (see, for example Leeuwen, P. W. N. M v. et al. 2000, 100, 2741-2769). Examples of suitable unsubstituted X groups include, but are not limited to, —$(CH_2)_n$—, 1,4'-ferrocene, 2,2'-diphenyl ether, 1,2-xylene and 4,5-xanthene. In a compound of Formula 7, each $R^9$, $R^{10}$, $R^{11}$ and $R^{12}$ is independently aryl or substituted aryl. Examples of aryl groups used herein include monocyclic aromatic hydrocarbons (such as phenyl) and oxygen-containing aromatic heterocycles (such as furyl). Examples of substituted aryl groups as used herein include aryl groups where one or more hydrogen of the aryl group has been replaced by an alkyl, alkoxy, chlorine, fluorine or fluoromethyl group (such as tolyl as xylyl).

Combinations of a palladium source and a ligand are generally selected to achieve high yields and high selectivity. Yield in the context of the present invention refers either the isolated yield or the calculated yield by area % (by HPLC analyses). Both isolated yield and calculated yield calculations are expressed as the moles of desired product formed divided by moles that would have been formed if there were no side reactions and the limiting reactant had reacted completely. Selectivity in the context of the present invention refers to moles of desired product formed divided by moles of undesired product formed. Combinations of a ligand and a palladium source are also selected on the basis of forming a homogeneous mixture. In the context of the present invention the palladium source is combined with an appropriate bidentate ligand. Of note for the present invention are bidentate bisphosphine ligands such as 1,4-bis(diphenylphosphino)butane (dppb), 1,1'-bis(diphenylphosphino)ferrocene, (dppf), 9,9-dimethyl-4,5-bis(diphenylphosphino)xanthene (XANTPHOS), and bis(2,2'-diphenylphosphinophenyl)ether (DPEphos), all of which are commercially available. Of particular note as an appropriate bidentate ligand is 1,1'-bis(diphenylphosphino)ferrocene, (dppf) for reasons of faster carbon monoxide uptake. Also of particular note as an appropriate bidentate ligand for reasons of cost is 1,4-bis(diphenylphosphino)butane (dppb). General methods for the preparation of other suitable bidentate bisphosphine ligands are described in the literature and are well known to those skilled in the art (see for example *Organometallics* 2008, 27, 5402-5422).

The palladium source and ligand may also be provided in the form of a pre-formed complex (i.e. of palladium source and ligand). Examples of pre-formed complexes of palladium (II) and bidentate bisphosphine ligand useful in the present invention include the commercially available dichloro[1,1'-bis(diphenylphosphino)ferrocene]palladium(II) dichloromethane adduct and dichloro(9,9-dimethyl-4,5-bis(diphenylphosphino)xanthene)palladium(II).

Alternatively, the palladium source and ligand may be combined separately. Examples of suitable palladium sources which can be utilized in this embodiment are palladium(II) carboxylates such as palladium(II) acetate, trifluoracetate, propionate, and benzoate; palladium salts of mineral acids, for example palladium(II) chloride, palladium(II) bromide, palladium(II) sulfate; and other palladium complexes such as (dibenzylideneacetone)dipalladium(0) and palladium(II) acetylacetonate, all of which are commercially available.

The most efficient utilization of the palladium source in the process of Scheme 1 is achieved by using an excess of the bidentate ligand relative to the palladium source. The molar ratio of bidentate ligand to palladium source can vary from 1 to 1 to 10 to 1, but is typically from 1.5-3.0 to 1.

The molar percentage of the palladium source relative to compounds of Formula 2 is not critical to overall selectivity but for practical use is preferably from 0.1% to 0.4%. Full conversion of a compound of Formula 2 to a compound of Formula 1 may be achieved in about 3 hours at 90° C. with a loading of 0.2 mol % palladium source relative to a compound of Formula 2.

The process of Scheme 1 produces a stoichiometric amount of HX (wherein X is Br or I) which is most conveniently neutralized by using at least a two-fold excess of the amine of Formula 3. Typical amounts of the amine of Formula 3 range from a 2× to 5× molar excess. The amine of Formula 3 can be introduced either as the substantially pure component as either a gas or liquid. Alternatively, a compound of Formula 3 can be introduced as a solution in a suitable solvent (preferably a suitable organic solvent or a mixture thereof) and most conveniently in the same suitable solvent used as the process solvent.

In general, any base compatible with the reaction mixture and conditions may be employed in the process of Scheme 1. Organic bases such as tertiary amines (e.g., triethylamine or tributylamine) are particularly suitable. Moreover, inorganic bases such as sodium carbonate or sodium bicarbonate; and hydroxides of sodium, calcium, cesium and potassium can also be employed.

The process of Scheme 1 is typically conducted in a suitable solvent. A variety of organic solvents are suitable as components of the solvent medium for the process. Examples of suitable solvents include organic solvents such as ethers, such as tetrahydrofuran and 2,5,8 trioxanonane (diglyme), nitriles such as acetonitrile and aromatic hydrocarbons such as xylenes or toluene, and mixtures thereof. Surprisingly, solvent systems that incorporate coordinating solvents such as ethylene glycol and N,N-dimethylethanolamine, either alone or in combination, are particularly advantageous in improving the selectivity and efficiency of the process of the present invention. When solvent mixtures containing ethylene glycol or N,N-dimethylethanolamine are used, an intermediate ester can be formed in-situ, but can be converted to the final compound of Formula 1 when exposed to a compound of Formula 3.

The total volume of the organic solvent used in the method of Scheme 1 is preferably between about 1 mL/g to about 20 mL/g relative to the weight of the compound of Formula 2, and more preferably between about 6 mL/g and about 10 mL/g Phosphine ligands are sensitive to the presence of both air and water in process of Scheme 1. Therefore the process is preferentially carried out in a substantially oxygen and water free solvent to prevent the formation of unwanted byproducts. Standard techniques can be used to obtain oxygen-free solvents including, for example, refluxing or distilling the solvents in an inert atmosphere such as nitrogen or argon, or sparging the solvents with an inert gas such as nitrogen or argon. Standard drying agents such as molecular sieves, potassium carbonate and magnesium sulfate may also be used.

The present method is carried out under a pressure of carbon monoxide. Most conveniently the reaction vessel is pressurized at room temperature. The pressure of carbon monoxide can vary between wide limits but relatively low pressure affords the best selectivity to compounds of Formula 1. Typically a pressure of between 20 and 100 psi (1.379e+005 and 6.895e+005 newtons/square meter) of carbon monoxide gives good results. More typically the range is between 40 and 90 psi (2.758e+005 and 6.205e+005 newtons/square meter) of carbon monoxide. The carbon monoxide required for the process of the present method is typically introduced in gaseous form as substantially pure or diluted with an inert gas such as nitrogen.

The method of Scheme 1 can be carried out using standard engineering practice. Preferably the reagents are charged to the reaction vessel in an oxygen-free environment. Standard techniques for obtaining an oxygen-free environment can be used, including, for example, evacuating the reaction vessel and re-pressurizing to atmospheric pressure with an inert gas. This method can be repeated two or more times to further reduce the oxygen present in the reaction vessel.

The reagents can be added to the reaction vessel in any order. One mode of addition involves adding the ligand and palladium source as a solid or slurry in a suitable solvent, followed by a compound of Formula 2 and a solution of a compound of Formula 3 in a suitable solvent. Any further solvent can then be added to accommodate the desired ratio of the mass of a compound of Formula 1 to the volume of the suitable solvent. The ligand, the palladium source the compound of Formula 2 can optionally be added as a solution or slurry in a suitable solvent. The compound of Formula 3 can optionally be added as the pure component, preferably after the other components of the reaction mixture have been added to the reaction vessel.

The method is typically conducted at a temperature between about 70° C. and 150° C. and more typically between about 90° C. and 120° C. Generally the best selectivity and yield of a compound of Formula 1 are obtained at the lowest temperature that gives practical reaction times. The reaction time may vary widely, ranging from a few minutes to several hours, depending on reaction conditions, palladium source, ligand and the particular compound of Formula 2 used. After the reaction, compounds of Formula 1 can be isolated by standard techniques known in the art, including filtration, extraction, evaporation, and crystallization. Optionally the reaction mixture may be washed with water followed by extraction of the aqueous phase with a suitable solvent (eg. ethyl acetate, toluene and lower alkyl ethers) prior to isolation of product. As the compounds of Formula 1 are typically solids at ambient temperature, they are often most easily isolated by filtration, optionally followed by washing with water and/or an organic solvent (e.g. xylenes, toluene or ethanol). Additional product can be isolated by concentrating the filtrate under reduced pressure, slurrying the resulting residue in an organic solvent (e.g. xylenes, toluene or ethanol), filtering and optionally washing with water and/or an organic solvent (e.g. xylenes, toluene or ethanol). The solid product can be further purified by recrystallization from an appropriate organic solvent (e.g. ethanol, methanol or acetonitrile).

As shown in Scheme 2, a useful embodiment of the present invention is a two-step method allowing for the preparation of a compound of Formula 1 by reacting a compound of Formula 2 with carbon monoxide and an alcohol of Formula 6 (wherein $R^8$ is $C_1$-$C_{14}$ alkyl, $C_2$-$C_{14}$ hydroxyalkyl, $C_3$-$C_{14}$ dialkylaminoalkyl, or $C_3$-$C_{14}$ halodialkylaminoalkyl) in the presence of a palladium source, a ligand and a base to yield a compound of Formula 4. The resulting ester of Formula 4 is then converted to a compound of Formula 1 by contacting with a compound of Formula 3 as depicted in Scheme 2. A compound of Formula 4 can be utilized without isolation and purification. Alternatively the compound of Formula 4 may be isolated, purified and converted into benzamides of Formula 1. Conditions for effecting this transformation (i.e., palladium source, ligand, etc.) are essentially the same as those described in Scheme 1 except that an alcohol of Formula 6 is used instead of an amine of Formula 3, which also functions as the reaction solvent. Methanol and ethylene glycol are particularly useful solvents in the process. Other organic co-solvents may be used as long as a large molar excess of the reactant alcohol is present in the reaction mixture.

Scheme 2

The compound of Formula 4 can optionally be isolated by standard techniques known in the art, including filtration, extraction, evaporation, and crystallization. The reaction mixture may be washed with water followed by extraction of the aqueous phase with a suitable organic solvent (ethyl acetate, toluene, ethers) prior to isolation of product. As the compounds of Formula 4 are typically solids at ambient temperature, they are often most easily isolated by filtration, optionally followed by washing with water and/or an organic solvent (xylenes, toluene, ethanol). Additional product can be isolated by concentrating the filtrate under reduced pressure, slurrying the resulting residue in an organic solvent (xylenes, toluene, ethanol), filtering and optionally washing with water and/or an organic solvent (xylenes, toluene, ethanol). The solid product can be further purified by recrystallization from an appropriate organic solvent (ethanol, methanol, acetonitrile).

Converting esters to amides (i.e. aminating) is known in the art. The method of Scheme 2 can be used to convert a compound of Formula 4 generated in-situ, (i.e. other than isolated) to a compound of Formula 1. Alternatively, a compound of Formula 4 can be isolated, and then converted by aminating a compound of Formula 1. Either method often involves heating the ester with the appropriate amine in a suitable solvent such as ethylene glycol or N,N-dimethylaminoethanol. A procedure useful for conversion of anthranilic esters to anthranilic amides is described in PCT Patent Publication WO 2006/062978. Also, E. B. Skibo et al., *Journal of Medicinal Chemistry* 2002, 45(25), 5543-5555 discloses the preparation of an anthranilic amide from the corresponding anthranilic ester using sodium cyanide catalyst.

The present method provides efficient means to produce aminobenzamides of Formula 1 or aminobenzoates Formula 4, typically in yields of 85-95%. Of particular note is that the present method can be used to provide remarkably high yields of compounds of Formula 1 in excellent purity even though these compounds as well as the starting compounds of Formula 2 contain amino substituents that can potentially participate in side reactions.

A compound of Formula 2 is generally known in the art, is commercially available or can be prepared from the literature. For example a compound of Formula 2 wherein $R^1$ is $CH_3$, $R^2$ is Cl and X is Br can be prepared as found in PCT Patent Publication WO 2008/051533 on page 93. A compound of Formula 2 wherein $R^1$ is $CH_3$, $R^2$ is cyano and X is Br can be prepared as found in PCT Patent Publication WO 2010/093191 on pages 83 and 84.

In another aspect of this invention, a compound of Formula 1 prepared by the method of the present invention can be useful as intermediates for preparing a compound of Formula 5 as shown in FIG. 2. Compounds of Formula 5 are useful as insecticides, as described, for example in PCT Patent Publication WO 2004/024222.

Figure 2

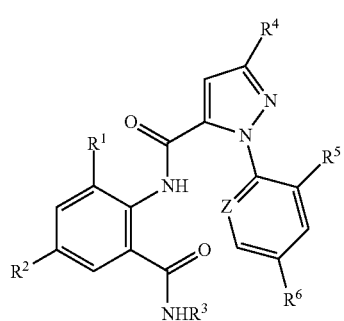

Of note is a compound of Formula 5 wherein $R^1$ is $C_1$-$C_4$ alkyl, $C_1$-$C_4$ haloalkyl, $C_1$-$C_4$ alkoxy or $C_1$-$C_6$ haloalkoxy; $R^2$ is F, Cl or cyano; $R^3$ is H, $C_1$-$C_4$ alkyl, $C_3$-$C_6$ cycloalkyl, $C_4$-$C_7$ cycloalkylalkyl, $C_4$-$C_7$ alkylcycloalkyl, or cyclopropylcyclopropyl; Z is $CR^7$ or N; $R^4$ is Cl, Br, $CF_3$, $OCHF_2$ or $OCH_2CF_3$; $R^5$ is F, Cl or Br; $R^6$ is H, F or Cl; and $R^7$ is H, F, Cl or Br. Of particular note is a compound of Formula 5 wherein $R^1$ is methyl; $R^2$ is Cl or cyano; $R^3$ is methyl; Z is N; $R^4$ is Br; and $R^6$ is H.

A variety of routes are possible for the preparation of a compound of Formula 5 from a compound of Formula 1. One such method is shown in Scheme 3. In this method a compound of Formula 5 is prepared by combining a compound of Formula 1, a pyrazole of Formula 8 and a sulfonyl chloride according to the general method taught in PCT Patent Publication WO 2006/062978.

Scheme 3

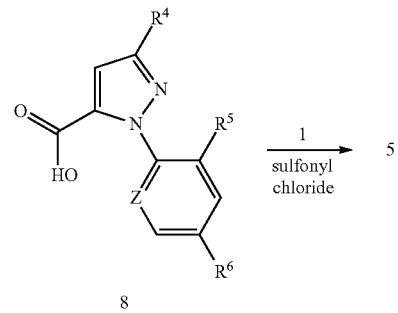

As described in WO 2006/062978, a variety of reaction conditions are possible for this transformation. Typically a sulfonyl chloride is added to a mixture of the compounds of Formulae 1 and 8 in the presence of a solvent and a base. Sulfonyl chlorides are generally of the formula $R^{13}S(O)_2Cl$ wherein $R^{13}$ is a carbon-based radical. Usually for this method $R^{13}$ is $C_1$-$C_4$ alkyl, $C_1$-$C_2$ haloalkyl, or phenyl optionally substituted with 1-3 substituents independently selected from the group consisting of halogen, $C_1$-$C_3$ alkyl and nitro. Commercially available sulfonyl chlorides include methanesulfonyl chloride ($R^{13}$ is $CH_3$), propanesulfonyl chloride ($R^{13}$ is $(CH_2)_2CH_3$), benzenesulfonyl chloride ($R^{13}$ is phenyl), and p-toluenesulfonyl chloride ($R^{13}$ is 4-methylphenyl). Methanesulfonyl chloride is of note for reasons of lower cost, ease of addition and/or less waste. At least one molar equivalent of the sulfonyl chloride per mole of the compound of Formula 8 is stoichiometrically needed for complete conversion. Typically the molar ratio of sulfonyl chloride to a compound of Formula 8 is no more than about 2.5, more typically no more than about 1.4.

The compound of Formula 5 is formed when the starting compounds of Formulae 1, 8 and the sulfonyl chloride are contacted with each other in a combined liquid phase, in which each is at least partially soluble. Since the starting materials of Formulae 1 and 8 are typically solids at ordinary ambient temperatures, the method is most satisfactorily conducted using a solvent in which the starting compounds have significant solubility. Thus typically the method is conducted in a liquid phase comprising a solvent. In some cases the carboxylic acid of Formula 8 may have only slight solubility, but its salt with added base may have more solubility in the solvent. Suitable solvents for this method include nitriles such as acetonitrile and propionitrile; esters such as methyl acetate, ethyl acetate and butyl acetate; ketones such as acetone, methyl ethyl ketone (MEK), and methyl butyl ketone; haloalkanes such as dichloromethane and trichloromethane; ethers such as ethyl ether, methyl tert-butyl ether, tetrahydrofuran (THF) and p-dioxane; aromatic hydrocarbons such as benzene, toluene, chlorobenzene, and dichlorobenzene; tertiary amines such as trialkylamines, dialkylanilines and optionally substituted pyridines; and mixtures of the foregoing. Solvents of note include acetonitrile, propionitrile, ethyl acetate, acetone, MEK, dichloromethane, methyl tert-butyl ether, THF, p-dioxane, toluene, and chlorobenzene. Of particular note as the solvent is acetonitrile, as it often provides products in superior yield and/or purity.

As the reaction of the present method generates hydrogen chloride as a byproduct, which would otherwise bind to basic centers on the compounds of Formulae 1, 5 and 8, the method is most satisfactorily conducted in the presence of at least one added base. The base can also facilitate constructive interaction of the carboxylic acid with the sulfonyl chloride compound and the anthranilamide. Reaction of an added base with the carboxylic acid of Formula 8 forms a salt, which may have greater solubility than the carboxylic acid in the reaction medium. Although the base may be added at the same time, in alternation, or even after the addition of the sulfonyl chloride, the base is typically added before the addition of the sulfonyl chloride. Some solvents such as tertiary amines also serve as bases, and when these are used as solvents they will be in large stoichiometric excess as bases. When the base is not used as the solvent the mole ratio of the base to the sulfonyl chloride is typically from about 2.0 to about 2.2, and is preferably from about 2.1 to about 2.2. Bases such as tertiary amines and substituted pyridines are useful in the present method. Of note are bases including 2-picoline, 3-picoline, 2,6-lutidine and pyridine. Of particular note as the base is 3-picoline, as its salts with carboxylic acid of a compound of Formula 8 are often highly soluble in solvents such as acetonitrile.

The compounds of Formula 5 can be isolated from the reaction mixtures by methods known to those skilled in the art, including crystallization, filtration and extraction. As disclosed in WO 2006/062978, in some cases under the coupling reaction conditions of Scheme 3 compounds of Formula 5 can partially cyclize to form iminobenzoxazine derivatives of Formula 9, as shown below in Scheme 4.

and Formula 5 compounds, and then treating the mixture with an aqueous acid solution, optionally in the presence of a suitable organic solvent (e.g., acetonitrile). WO 2006/062978 discloses specific examples relevant to the method of Scheme 6, including examples illustrating treatment of the reaction mixture with an aqueous acid solution prior to isolating compounds of Formula 5.

Alternatively, compounds of Formula 9 can be converted back to compounds of Formula 5 prior to isolation by contacting the reaction mixture with water and heating. Typically, the conversion of Formula 9 compounds to Formula 5 compounds can be achieved by adding between about 2 to 6 parts by weight of water relative to the weight of the starting compound of Formula 1 and then heating to between about 45 and about 65° C. The conversion of the compound of Formula 9 to the compound of Formula 5 is usually complete in 1 h or less.

Pyrazole-5-carboxylic acids of Formula 8 can be prepared from 5-oxo-3-pyrazolidinecarboxylates by treatment with a halogenating agent to give 3-halo-4,5-dihydro-1H-pyrazole-5-carboxylates, which can subsequently be treated with an oxidizing agent to provide esters of pyrazole carboxylic acid of Formula 8. The esters can then be converted to the acids (i.e. a compound of Formula 8). Halogenating agents that can be used include, for example, phosphorus oxyhalides, phosphorus trihalides, phosphorus pentahalides, thionyl chloride, dihalotrialkylphosphoranes, dihalodiphenylphosphoranes, oxalyl chloride and phosgene. The oxidizing agents can be, for example, hydrogen peroxide, organic peroxides, potassium persulfate, sodium persulfate, ammonium persulfate, potassium monopersulfate (e.g., Oxone®), elemental bromine or potassium permanganate. See PCT Patent Publications WO 2003/016283, WO 2004/087689 and WO 2004/011453 for a description of the halogenation and oxidation methods, and a procedure for preparing the starting 5-oxo-3-pyrazolidinecarboxylates. To convert the esters to carboxylic acids a variety of methods reported in the chemical literature can be used, including nucleophilic cleavage under anhydrous conditions or hydrolysis involving the use of either acids or bases (see T. W. Greene and P. G. M. Wuts, *Protective Groups in Organic Synthesis,* 2nd ed., John Wiley & Sons, Inc., New York, 1991, pp. 224-269 for a review of methods).

Scheme 4

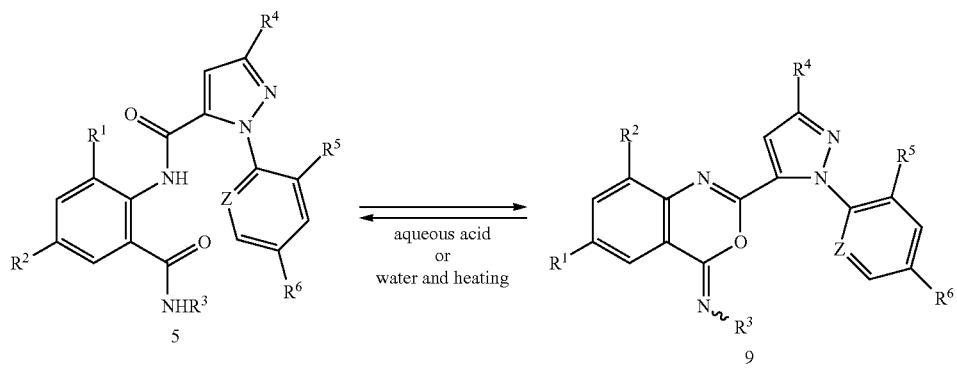

As discussed in WO 2006/062978, in these cases it is often advantageous to convert the iminobenzoxazine compounds of Formula 9 back to the amides of Formula 5 prior to isolation. This conversion can be accomplished by treatment of the reaction mixture with an aqueous acid solution (e.g., aqueous hydrochloric acid); or by isolating the mixture of Formula 9

Base-catalyzed hydrolytic methods are preferred to prepare the carboxylic acids of Formula 8 from the corresponding esters. Suitable bases include alkali metal hydroxides (such as lithium, sodium, or potassium hydroxides). For example, the esters can be dissolved in a mixture of water and alcohol such as methanol. Upon treatment with sodium hydroxide or potassium hydroxide, the esters saponify to provide the sodium or potassium salt of the carboxylic acid. Acidification with a strong acid, such as hydrochloric acid or sulfuric acid, gives the carboxylic acids. PCT Patent Publication WO 2003/016283 provides a relevant experimental example illustrating the base-catalyzed hydrolysis method for the conversion of an ester to an acid.

Alternatively, a compound of Formula 8 can be prepared from 4,5-dihydro-5-hydroxy-1H-pyrazole-5-carboxylates via an acid-catalyzed dehydration reaction to give esters, which can then be converted to acids of Formula 8. Typical reaction conditions involve treatment of 4,5-dihydro-5-hydroxy-1H-pyrazole-5-carboxylates with an acid, for example, sulfuric acid, in an organic solvent, such as acetic acid, at temperatures between about 0 and 100° C. The method is described PCT Patent Publication WO 2003/016282. Conversion of the esters to acids can be done using the methods described above. Also, WO 2003/016282 provides a relevant experimental example for the conversion of an ester to an acid.

Without further elaboration, it is believed that one skilled in the art using the preceding description can utilize the present invention to its fullest extent. The following Examples are, therefore, to be construed as merely illustrative and not limiting of the disclosure in any way whatsoever. $^1$H NMR spectra are reported in ppm downfield from tetramethylsilane; s is singlet, d is doublet, m is multiplet. HPLC analyses of the reaction mixtures and products were performed using an Ace 3 C18 Ultra Inert® chromatography column (reversed phase column manufactured by MacMod Analytical Inc., Chadds Ford, Pa., 19317; 3 μm particle size, 4.6 mm diameter×15 cm length; catalog number Ace111-1546) with an eluent of 5-80% acetonitrile/pH 3 phosphate buffer.

Without further elaboration, it is believed that one skilled in the art using the preceding description can utilize the present invention to its fullest extent. The following Examples are, therefore, to be construed as merely illustrative, and not limiting of the disclosure in any way whatsoever. The method in the following Examples illustrate a procedure for each step in an overall synthetic transformation, and the starting material for each step may or may not have necessarily been prepared by a particular preparative run whose procedure is described in other Examples or Steps. In the following Examples and Tables "Exp." stands for experiment. $^1$H NMR spectra is reported in ppm downfield from tetramethylsilane at 400 MHz unless otherwise noted; "s" means singlet, "m" means multiplet, "d" means doublet.

Example 1

Preparation of
2-amino-5-chloro-N,3-dimethylbenzamide
(Compound 1a)

A 100 mL Hastelloy-C pressure-rated reactor (Reactor 1) fitted with an overhead stirrer, a thermocouple, a pressure transducer, a sample tube and a gas inlet tube was charged with 4.1 g of 2-bromo-4-chloro-6-methylbenzeneamine (Compound 2a) (97 wt %, 18.0 mmol), 0.0083 g of palladium (II) acetate (98 wt %, 0.0361 mmol, 0.002 eq.) and 0.0317 g of 1,4-bis(diphenylphosphino)butane (dppb) (98 wt %, 0.0721 mmol, 0.004 eq.). The reactor was twice sealed, pressurized (to 2.4 atm with nitrogen) and then vented. Following an acceptable leak test, Reactor 1 was vented to the atmosphere and then sealed. A separate but identical reactor (Reactor 2), was then charged with approximately 60 g of ethylene glycol. Reactor 2 was sealed and then, without agitation, nitrogen pressure was applied to discharge all of the ethylene glycol except that which lay below the bottom of the sample tube; the discharged ethylene glycol was discarded. Reactor 2 was opened and 55.5 g of fresh ethylene glycol was added. Reactor 2 was sealed again and pressurized with nitrogen to 3.4 atm and vented. After repeating this twice, agitation was started in Reactor 2 and with the vent open to an oil bubbler, nitrogen was sparged into the ethylene glycol through the sample tube for approximately 97 minutes. Nitrogen flow and agitation was stopped and Reactor 2 was sealed. The pressure in both reactors was approximately 1 atm. The sample tube of Reactor 2 was connected to the sample tube on Reactor 1 with pressure-rated, translucent, ⅛-inch Teflon® tubing. Ethylene glycol was transferred from Reactor 2 to Reactor 1 by applying 3.4 atm nitrogen pressure to Reactor 2. After the transfer was complete, as determined by the absence of liquid seen in the Teflon® transfer tube, Reactor 1 was sealed, Reactor 2 was vented and the tube connecting the two reactors was removed. Agitation in Reactor 1 was started. The temperature in Reactor 1 was maintained at approximately 25° C. by a combination of jacket fluid set at 20° C. and electrical resistance heating, both of which were controlled by computer. The nitrogen atmosphere in Reactor 1 was replaced with carbon monoxide by pressurizing Reactor 1 to 3.74 atm from a cylinder of compressed CO and then venting to atmosphere in three successive cycles.

A lecture bottle of pressurized anhydrous methylamine was placed in a stand on top of a balance and the bottle was connected to Reactor 1 with stainless steel tubing. A total of 6.86 g of methylamine (98 wt %, 216 mmol, 12 eq.) was charged to Reactor 1 over approximately 18 minutes. The addition of methylamine was found to be exothermic and The contents of Reactor 1 briefly reached 37° C. After the methylamine was added, Reactor 1 was sealed and heated to 110° C. by computer control. The methylamine cylinder was disconnected and the CO cylinder was reconnected to Reactor 1. After the Reactor 1 reached 110° C., CO was fed to Reactor 1 to maintain 3.74 atm using a computer controlled flow meter; the amount of CO gas fed to the reactor was recorded. After 60 min, a sample was taken for HPLC analysis. The pressure and temperature were maintained for 25 h although after 3.8 h, 1.1 eq of CO had been fed to Reactor 1. At this point, the CO flow to the reactor substantially subsided. Reactor 1 was then cooled to 25° C. and made inert with nitrogen as described above. The contents of Reactor 1 were transferred to a glass bottle, sampled for HPLC analysis and then sealed.

After four days stored at ambient temperature, 57.13 g of the reaction mixture were transferred to a 200 mL single-neck round bottom flask equipped with a magnetic stir bar. An additional funnel was attached to the round bottom flask and, with agitation, 50 mL de-ionized water was added to the flask over approximately 23 minutes. After approximately 11 mL of de-ionized water was added, the mixture turned from a clear solution to a thick slurry. The mixture was filtered and the solid product cake washed with 50 mL of de-ionized water. A total of 4.92 g of product was obtained, and this was dried in a vacuum oven at approximately 70° C., under vacuum for six days to afford 2.36 g of the title compound with an assay of 99.1 wt % (corresponding to an approximate isolated yield of 70%).

Example 2

Preparation of 2-amino-5-chloro-N,3-dimethylbenzamide

Step A: Preparation of 2-hydroxyethyl 2-amino-5-chloro-3-methylbenzoate (Compound 4a) and 2-(dimethylamino)ethyl 2-amino-5-chloro-3-methylbenzoate (Compound 4b)

A 100 mL Hastelloy-C pressure-rated reactor (Reactor 1), fitted with overhead stirring, a thermocouple, a pressure transducer, a sample tube and a gas inlet tube was charged with 8.2 g of 2-bromo-4-chloro-6-methylbenzeneamine (97 wt %, 36.1 mmol), 0.0165 g of palladium(II) acetate (98 wt %, 0.0721 mmol, 0.002 eq.) and 0.0634 g of 1,4-bis(diphenylphosphino)butane (dppb) (98 wt %, 0.144 mmol, 0.004 eq.). The reactor was twice sealed, pressurized (to 2.4 atm with nitrogen) and then vented. Following an acceptable leak test, Reactor 1 was vented to the atmosphere and then sealed. In a separate but identical reactor (Reactor 2) approximately 30 mL of a mixture containing 78.8 wt % ethylene glycol and 21.2 wt % 2-dimethylaminoethanol were charged. Reactor 2 was sealed and then, without agitation, nitrogen pressure was applied to the reactor to discharge all of the mixture except that which lay below the bottom of the sample tube; the discharged liquid was discarded. Reactor 2 was opened and 52.8 g of the same solvent mixture was charged, (i.e. with approximately 41.6 g ethylene glycol and 11.2 g of 2-dimethylaminoethanol (124.8 mmol 3.46 eq relative to 2-bromo-4-chloro-6-methylbenzeneamine)). Reactor 2 was then sealed, pressurized (to 3.4 atm with nitrogen) and vented. This process was repeated twice. Next, agitation was started in Reactor 2 and with the vent open to an oil bubbler, nitrogen was sparged into the mixture through the sample tube for approximately 15 minutes. Nitrogen flow and agitation was stopped and Reactor 2 was sealed. The pressure in both reactors was approximately 1 atm. The sample tube of Reactor 2 was connected to the sample tube on Reactor 1 with pressure-rated, translucent, ⅛-inch (0.3175 centimeter) Teflon® tubing. The mixture in Reactor 2 was transferred to Reactor 1 by applying 3.4 atm nitrogen pressure to Reactor 2. After the transfer was complete, as determined by the absence of liquid seen in the Teflon® transfer tube, Reactor 1 was sealed and agitation initiated. The temperature in Reactor 1 was maintained at approximately 25° C. by a combination of jacket fluid set at 20° C. and electrical resistance heating, both of which were controlled by computer. The nitrogen atmosphere in Reactor 1 was replaced with carbon monoxide by pressurizing Reactor 1 to 3.74 atm from a cylinder of compressed CO and then venting to atmosphere in three successive cycles.

Reactor 1 was heated to 110° C. by computer control. When the temperature in Reactor 1 reached approximately 93° C., CO was fed to the reactor to maintain 1.36 atm pressure. When the temperature reached 100° C., CO pressure was maintained at 5.1 atm. The contents of Reactor 1 were allowed to mix at 110° C. and 5.1 atm for approximately 300 minutes, during which time small samples were withdrawn approximately every hour for HPLC analysis. After this time, Reactor 1 was cooled to 30° C. and the CO pressure was vented to 1.36 atm. Reactor 1 was held at these conditions overnight. HPLC Area % (i.e. A %) analyses of the samples are shown in Table A.

TABLE A

| Time (min) | 1a (A %) | 2a (A %) | 4a (A %) | 4b (A %) |
|---|---|---|---|---|
| 60 | 0 | 4.71 | 76.8 | 10.4 |
| 120 | 0 | 0.63 | 83.7 | 8.48 |
| 180 | 0 | 0.15 | 85.4 | 8.05 |
| 240 | 0 | 0 | 85.8 | 7.53 |
| 300 | 0 | 0 | 86.0 | 7.61 |

1a: 2-amino-5-chloro-N,3-dimethylbenzamide,
2a: 2-bromo-4-chloro-6-methylbenzeneamine,
4a: 2-hydroxyethyl 2-amino-5-chloro-3-methylbenzoate,
4b: 2-(dimethylamino)ethyl 2-amino-5-chloro-3-methylbenzoate.

Step B: Preparation of 2-amino-5-chloro-N,3-dimethylbenzamide (Compound 1a)

The CO cylinder was disconnected from Reactor 1 from Step A above. A lecture bottle of pressurized anhydrous methylamine was placed in a stand on top of a balance and the bottle was connected to Reactor 1 with coiled stainless steel tubing. After venting Reactor 1 to approximately 1 atm, a total of 5.72 g of methylamine (98 wt %, 180 mmol, 5 eq.) was charged to Reactor 1 over approximately eleven minutes. The addition of methylamine was found to be exothermic. After the methylamine was added, Reactor 1 was sealed and heated to 110° C. by computer control. The methylamine cylinder was disconnected and a cylinder of compressed nitrogen was connected to Reactor 1. After the Reactor 1 reached 110° C., nitrogen was fed to Reactor 1 to maintain 5.1 atm using a computer controlled flow meter. Small samples were withdrawn approximately every hour for HPLC analysis. After 364 min, Reactor 1 was then cooled to 30° C. and rendered inert with nitrogen as described above. The contents of Reactor 1 were transferred to a glass bottle and sealed. HPLC Area % (i.e. A %) analyses of the samples are shown in Table B.

TABLE B

| Time (min) | 1a (A %) | 2a (A %) | 4a (A %) | 4b (A %) |
|---|---|---|---|---|
| 60 | 48.3 | 0 | 39.3 | 3.77 |
| 120 | 72.0 | 0 | 17.7 | 1.61 |
| 180 | 82.0 | 0 | 7.79 | 0.70 |
| 240 | 85.3 | 0 | 4.14 | 0.38 |
| 300 | 87.9 | 0 | 1.88 | 0 |
| 360 | 88.2 | 0 | 0.94 | 0 |

1a: 2-amino-5-chloro-N,3-dimethylbenzamide,
2a: 2-bromo-4-chloro-6-methylbenzeneamine,
4a: 2-hydroxyethyl 2-amino-5-chloro-3-methylbenzoate,
4b: 2-(dimethylamino)ethyl 2-amino-5-chloro-3-methylbenzoate.

Example 3

Three additional experiments were conducted following the method described in Example 2 above except that the ratio of ethylene glycol to 2-dimethylaminoethanol was varied as shown in Table C. Each experiment was run at a constant volume of approximately 50 mL. The combined weight of ethylene glycol and 2-dimethylaminoethanol varies among the experiments to compensate for the variation in mixture densities.

TABLE C

| Reagent | Example 2 | Exp. B | Exp. C | Exp. D |
|---|---|---|---|---|
| 2a (g) | 8.2 | 8.2 | 8.2 | 8.2 |
| Pd(OAc)$_2$ (g) | 0.0165 | 0.0165 | 0.0165 | 0.0165 |

TABLE C-continued

| Reagent | Example 2 | Exp. B | Exp. C | Exp. D |
|---|---|---|---|---|
| dppb (g) | 0.0634 | 0.0634 | 0.0634 | 0.0634 |
| ethylene glycol (g) | 41.6 | 0 | 27.8 | 55.5 |
| 2-dimethylaminoethanol (g) | 11.2 | 44.7 | 22.4 | 3.6 |
| (mol. eq) | (3.5) | (13.8) | (6.9) | (1.1) |
| Temperature (° C.) | 110 | 100 | 110 | 110 |

2a: 2-bromo-4-chloro-6-methylbenzeneamine.

Table D shows the conversion of 2a as a function of time for all four experiments, expressed in Area % of 2a.

TABLE D

| Time (min) | Example 2 | Exp. B | Exp. C | Exp. D |
|---|---|---|---|---|
| 60 | 4.71 | 31.4 | 21.7 | 12.1 |
| 120 | 0.63 | 17.2 | 5.63 | 5.84 |
| 180 | 0.15 | 10.5 | 2.56 | 3.93 |
| 240 | 0 | — | 0.83 | 3.07 |
| 300 | 0 | 10.5 | 0.35 | 2.67 |

Table D shows that 2a was fully consumed during the carbonylation in Example 2 in which 3.5 eq 2-dimethylaminoethanol was used. The rate of conversion of 2a was greater than that of the other experiments when less (Experiment D) or more (Experiment C) 2-dimethylaminoethanol used. When methylamine was added to each experiment, any remaining 2a was consumed.

Table E shows the HPLC Area % analysis of the final reaction solution for each of the four experiments.

TABLE E

| Compound | Example 2 | Exp. B | Exp. C | Exp. D |
|---|---|---|---|---|
| 1a (Area %) | 88.2 | 84.9 | 89.7 | 86.4 |

Example 4

Step A: Preparation of 3-bromo-N-[4-chloro-2-methyl-6-[(methylamino)carbonyl]phenyl]-1-(3-chloro-2-pyridinyl)-1H-pyrazole-5-carboxamide To a mixture of 3-bromo-1-(3-chloro-2-pyridinyl)-1H-pyrazole-5-carboxylic acid (see PCT Patent Publication WO 03/015519 for preparation) (93.6% purity, 16.16 g, 50.0 mmol) and 2-amino-5-chloro-N,3-dimethylbenzamide (i.e. the product of Examples 1, 2 or 3) (10.43 g, 52.5 mmol) in acetonitrile (35 mL) was added 3-picoline (12.65 mL, 12.11 g, 130 mmol). The mixture was cooled to −5° C., and then a solution of methanesulfonyl chloride (4.64 mL, 6.89 g, 60 mmol) in acetonitrile (10 mL) was added dropwise at −5 to 0° C. The mixture was stirred for 15 minutes at this temperature, and then for 3 h at room temperature. Then water (15 mL) was added dropwise and the mixture was cooled to 0° C. for 1 h. The mixture was filtered, and the solids were washed with 3:1 acetonitrile-water (2×10 mL), and then with acetonitrile (2×10 mL), and dried under nitrogen to afford the title compound as a light tan powder, 23.98 g (92.9% uncorrected yield), m.p. 239-240° C.

$^1$H NMR (CDCl$_3$) δ 2.18 (s, 3H), 2.95 (s, 3H), 6.21 (m, 1H), 7.10 (s, 1H), 7.24 (m, 2H), 7.39 (m, 1H), 7.80 (d, 1H), 8.45 (d, 1H).

By the procedures described herein together with methods known in the art, the compounds disclosed in the Tables that follow can be prepared. In Table 1 and the following tables: t means tertiary, s means secondary, n means normal, i means iso, c means cyclo, Me means methyl, Et means ethyl, Pr means propyl, and Bu means butyl. Concatenations of groups are abbreviated similarly; for example, "c-PrCH$_2$" means cyclopropylmethyl.

TABLE 1

$R^1$ is Me, $R^2$ is Cl

| $R^3$ | $R^3$ | $R^3$ | $R^3$ |
|---|---|---|---|
| H | n-Bu | c-Bu | 2-CH$_3$—c-Pr |
| Me | i-Bu | c-pentyl | 1,1'-bicyclopropyl-2-yl |
| Et | s-Bu | c-hexyl | 1,1'-bicyclopropyl-1-yl |
| n-Pr | t-Bu | c-PrCH$_2$ | (1R,2S)-1,1'-bicyclopropyl-2-yl |
| i-Pr | c-Pr | 1-CH$_3$—c-Pr | (1R,2R)-1,1'-bicyclopropyl-2-yl |

The present disclosure also includes Tables 1A through 41A, each of which is constructed the same as Table 1 above, except that the table heading in Table 1 (i.e $R^1$ is Me, $R^2$ is CO is replaced with the respective table heading shown below. For Example, in Table 1A the table heading is "$R^1$ is Me, $R^2$ is F", and $R^3$ is as defined in Table 1 above. Thus, the first entry in Table 1A specifically discloses 2-amino-5-fluoro-3-methylbenzamide. Tables 2A through 41A are constructed similarly.

| Table | Row Heading |
|---|---|
| 1A | $R^1$ is Me, $R^2$ is F |
| 2A | $R^1$ is Me, $R^2$ is CN |
| 3A | $R^1$ is Et, $R^2$ is Cl |
| 4A | $R^1$ is Et, $R^2$ is F |
| 5A | $R^1$ is Et, $R^2$ is CN |
| 6A | $R^1$ is n-Pr, $R^2$ is Cl |
| 7A | $R^1$ is n-Pr, $R^2$ is F |
| 8A | $R^1$ is n-Pr, $R^2$ is CN |
| 9A | $R^1$ is i-Pr, $R^2$ is Cl |
| 10A | $R^1$ is i-Pr, $R^2$ is F |
| 11A | $R^1$ is i-Pr, $R^2$ is CN |
| 12A | $R^1$ is n-Bu, $R^2$ is Cl |
| 13A | $R^1$ is n-Bu, $R^2$ is F |
| 14A | $R^1$ is n-Bu, $R^2$ is CN |
| 15A | $R^1$ is i-Bu, $R^2$ is Cl |
| 16A | $R^1$ is i-Bu, $R^2$ is F |
| 17A | $R^1$ is i-Bu, $R^2$ is CN |
| 18A | $R^1$ is s-Bu, $R^2$ is Cl |
| 19A | $R^1$ is s-Bu, $R^2$ is F |
| 20A | $R^1$ is s-Bu, $R^2$ is CN |
| 21A | $R^1$ is t-Bu, $R^2$ is Cl |
| 22A | $R^1$ is t-Bu, $R^2$ is F |
| 23A | $R^1$ is t-Bu, $R^2$ is CN |
| 24A | $R^1$ is CF$_3$, $R^2$ is Cl |
| 25A | $R^1$ is CF$_3$, $R^2$ is F |
| 26A | $R^1$ is CF$_3$, $R^2$ is CN |
| 27A | $R^1$ is CH$_2$CF$_3$, $R^2$ is Cl |
| 28A | $R^1$ is CH$_2$CF$_3$, $R^2$ is F |
| 29A | $R^1$ is CH$_2$CF$_3$, $R^2$ is CN |
| 30A | $R^1$ is OMe, $R^2$ is Cl |
| 31A | $R^1$ is OMe, $R^2$ is F |
| 32A | $R^1$ is OMe, $R^2$ is CN |
| 33A | $R^1$ is OEt, $R^2$ is Cl |
| 34A | $R^1$ is OEt, $R^2$ is F |
| 35A | $R^1$ is OEt, $R^2$ is CN |

-continued

| Table | Row Heading |
|---|---|
| 36A | $R^1$ is $OCF_3$, $R^2$ is Cl |
| 37A | $R^1$ is $OCF_3$, $R^2$ is F |
| 38A | $R^1$ is $OCF_3$, $R^2$ is CN |
| 39A | $R^1$ is $OCH_2CF_3$, $R^2$ is Cl |
| 40A | $R^1$ is $OCH_2CF_3$, $R^2$ is F |
| 41A | $R^1$ is $OCH_2CF_3$, $R^2$ is CN |

Table 2 illustrates particular transformations to prepare a compound of Formula 5 from a compound of Formulae 1 and 8 according to a method of the present invention.

TABLE 2

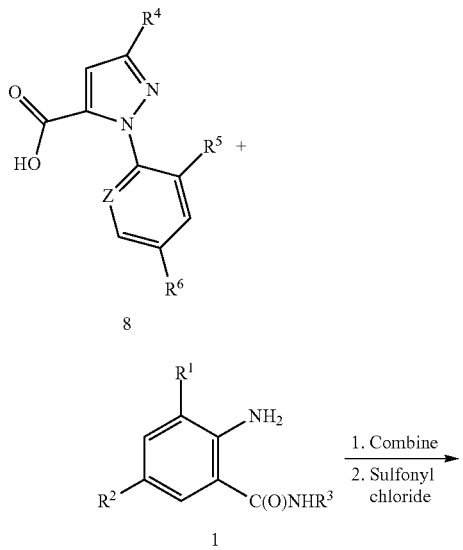

| $R^1$ | $R^2$ | $R^3$ | $R^4$ | Z | $R^5$ |
|---|---|---|---|---|---|
| $CH_3$ | Cl | H | $CF_3$ | N | F |
| $CH_3$ | Cl | Me | $CF_3$ | N | F |
| $CH_3$ | Cl | Et | $CF_3$ | N | F |
| $CH_3$ | Cl | i-Pr | $CF_3$ | N | F |
| $CH_3$ | Cl | t-Bu | $CF_3$ | N | F |
| $CH_3$ | Cl | H | $CF_3$ | N | Cl |
| $CH_3$ | Cl | Me | $CF_3$ | N | Cl |
| $CH_3$ | Cl | Et | $CF_3$ | N | Cl |
| $CH_3$ | Cl | i-Pr | $CF_3$ | N | Cl |
| $CH_3$ | Cl | t-Bu | $CF_3$ | N | Cl |
| $CH_3$ | Cl | H | $CF_3$ | N | Br |
| $CH_3$ | Cl | Me | $CF_3$ | N | Br |
| $CH_3$ | Cl | Et | $CF_3$ | N | Br |
| $CH_3$ | Cl | i-Pr | $CF_3$ | N | Br |
| $CH_3$ | Cl | t-Bu | $CF_3$ | N | Br |
| $CH_3$ | Cl | H | Cl | N | F |
| $CH_3$ | Cl | Me | Cl | N | F |
| $CH_3$ | Cl | Et | Cl | N | F |
| $CH_3$ | Cl | i-Pr | Cl | N | F |
| $CH_3$ | Cl | t-Bu | Cl | N | F |
| $CH_3$ | Cl | H | Cl | N | Cl |
| $CH_3$ | Cl | Me | Cl | N | Cl |
| $CH_3$ | Cl | Et | Cl | N | Cl |
| $CH_3$ | Cl | i-Pr | Cl | N | Cl |
| $CH_3$ | Cl | i-Bu | Cl | N | Cl |
| $CH_3$ | Cl | H | Cl | N | Br |
| $CH_3$ | Cl | Me | Cl | N | Br |
| $CH_3$ | Cl | Et | Cl | N | Br |
| $CH_3$ | Cl | i-Pr | Cl | N | Br |
| $CH_3$ | Cl | t-Bu | Cl | N | Br |
| $CH_3$ | Cl | H | Br | N | F |
| $CH_3$ | Cl | Me | Br | N | F |
| $CH_3$ | Cl | Et | Br | N | F |
| $CH_3$ | Cl | i-Pr | Br | N | F |
| $CH_3$ | Cl | t-Bu | Br | N | F |
| $CH_3$ | Cl | H | Br | N | Cl |
| $CH_3$ | Cl | Me | Br | N | Cl |
| $CH_3$ | Cl | Et | Br | N | Cl |
| $CH_3$ | Cl | i-Pr | Br | N | Cl |
| $CH_3$ | Cl | t-Bu | Br | N | Cl |
| $CH_3$ | Cl | H | Br | N | Br |
| $CH_3$ | Cl | Me | Br | N | Br |
| $CH_3$ | Cl | Et | Br | N | Br |
| $CH_3$ | Cl | i-Pr | Br | N | Br |
| $CH_3$ | Cl | t-Bu | Br | N | Br |
| $CH_3$ | Cl | H | $OCH_2CF_3$ | N | F |
| $CH_3$ | Cl | Me | $OCH_2CF_3$ | N | F |
| $CH_3$ | Cl | Et | $OCH_2CF_3$ | N | F |
| $CH_3$ | Cl | i-Pr | $OCH_2CF_3$ | N | F |
| $CH_3$ | Cl | t-Bu | $OCH_2CF_3$ | N | F |
| $CH_3$ | Cl | H | $OCH_2CF_3$ | N | Cl |
| $CH_3$ | Cl | Me | $OCH_2CF_3$ | N | Cl |
| $CH_3$ | Cl | Et | $OCH_2CF_3$ | N | Cl |
| $CH_3$ | Cl | i-Pr | $OCH_2CF_3$ | N | Cl |
| $CH_3$ | Cl | t-Bu | $OCH_2CF_3$ | N | Cl |
| $CH_3$ | Cl | H | $OCH_2CF_3$ | N | Br |
| $CH_3$ | Cl | Me | $OCH_2CF_3$ | N | Br |
| $CH_3$ | Cl | Et | $OCH_2CF_3$ | N | Br |
| $CH_3$ | Cl | i-Pr | $OCH_2CF_3$ | N | Br |
| $CH_3$ | Cl | t-Bu | $OCH_2CF_3$ | N | Br |
| $CH_3$ | Cl | H | $OCHF_2$ | N | F |
| $CH_3$ | Cl | Me | $OCHF_2$ | N | F |
| $CH_3$ | Cl | Et | $OCHF_2$ | N | F |
| $CH_3$ | Cl | i-Pr | $OCHF_2$ | N | F |
| $CH_3$ | Cl | t-Bu | $OCHF_2$ | N | F |
| $CH_3$ | Cl | H | $OCHF_2$ | N | Cl |
| $CH_3$ | Cl | Me | $OCHF_2$ | N | Cl |
| $CH_3$ | Cl | Et | $OCHF_2$ | N | Cl |
| $CH_3$ | Cl | i-Pr | $OCHF_2$ | N | Cl |
| $CH_3$ | Cl | t-Bu | $OCHF_2$ | N | Cl |
| $CH_3$ | Cl | H | $OCHF_2$ | N | Br |
| $CH_3$ | Cl | Me | $OCHF_2$ | N | Br |
| $CH_3$ | Cl | Et | $OCHF_2$ | N | Br |
| $CH_3$ | Cl | i-Pr | $OCHF_2$ | N | Br |
| $CH_3$ | Cl | t-Bu | $OCHF_2$ | N | Br |
| $CH_3$ | Cl | H | $CF_3$ | CH | F |
| $CH_3$ | Cl | Me | $CF_3$ | CH | F |
| $CH_3$ | Cl | Et | $CF_3$ | CH | F |
| $CH_3$ | Cl | i-Pr | $CF_3$ | CH | F |
| $CH_3$ | Cl | t-Bu | $CF_3$ | CH | F |
| $CH_3$ | Cl | H | $CF_3$ | CH | Cl |
| $CH_3$ | Cl | Me | $CF_3$ | CH | Cl |
| $CH_3$ | Cl | Et | $CF_3$ | CH | Cl |
| $CH_3$ | Cl | i-Pr | $CF_3$ | CH | Cl |
| $CH_3$ | Cl | t-Bu | $CF_3$ | CH | Cl |
| $CH_3$ | Cl | H | $CF_3$ | CH | Br |
| $CH_3$ | Cl | Me | $CF_3$ | CH | Br |
| $CH_3$ | Cl | Et | $CF_3$ | CH | Br |
| $CH_3$ | Cl | i-Pr | $CF_3$ | CH | Br |
| $CH_3$ | Cl | t-Bu | $CF_3$ | CH | Br |
| $CH_3$ | Cl | H | Cl | CH | F |
| $CH_3$ | Cl | Me | Cl | CH | F |
| $CH_3$ | Cl | Et | Cl | CH | F |
| $CH_3$ | Cl | i-Pr | Cl | CH | F |
| $CH_3$ | Cl | t-Bu | Cl | CH | F |
| $CH_3$ | Cl | H | Cl | CH | Cl |

TABLE 2-continued

| | | | | | |
|---|---|---|---|---|---|
| CH₃ | Cl | Me | Cl | CH | Cl |
| CH₃ | Cl | Et | Cl | CH | Cl |
| CH₃ | Cl | i-Pr | Cl | CH | Cl |
| CH₃ | Cl | t-Bu | Cl | CH | Cl |
| CH₃ | Cl | H | Cl | CH | Br |
| CH₃ | Cl | Me | Cl | CH | Br |
| CH₃ | Cl | Et | Cl | CH | Br |
| CH₃ | Cl | i-Pr | Cl | CH | Br |
| CH₃ | Cl | t-Bu | Cl | CH | Br |
| CH₃ | Cl | H | Br | CH | F |
| CH₃ | Cl | Me | Br | CH | F |
| CH₃ | Cl | Et | Br | CH | F |
| CH₃ | Cl | i-Pr | Br | CH | F |
| CH₃ | Cl | t-Bu | Br | CH | F |
| CH₃ | Cl | H | Br | CH | Cl |
| CH₃ | Cl | Me | Br | CH | Cl |
| CH₃ | Cl | Et | Br | CH | Cl |
| CH₃ | Cl | i-Pr | Br | CH | Cl |
| CH₃ | Cl | t-Bu | Br | CH | Cl |
| CH₃ | Cl | H | Br | CH | Br |
| CH₃ | Cl | Me | Br | CH | Br |
| CH₃ | Cl | Et | Br | CH | Br |
| CH₃ | Cl | i-Pr | Br | CH | Br |
| CH₃ | Cl | t-Bu | Br | CH | Br |
| CH₃ | Cl | H | OCH₂CF₃ | CH | F |
| CH₃ | Cl | Me | OCH₂CF₃ | CH | F |
| CH₃ | Cl | Et | OCH₂CF₃ | CH | F |
| CH₃ | Cl | i-Pr | OCH₂CF₃ | CH | F |
| CH₃ | Cl | t-Bu | OCH₂CF₃ | CH | F |
| CH₃ | Cl | H | OCH₂CF₃ | CH | Cl |
| CH₃ | Cl | Me | OCH₂CF₃ | CH | Cl |
| CH₃ | Cl | Et | OCH₂CF₃ | CH | Cl |
| CH₃ | Cl | i-Pr | OCH₂CF₃ | CH | Cl |
| CH₃ | Cl | t-Bu | OCH₂CF₃ | CH | Cl |
| CH₃ | Cl | H | OCH₂CF₃ | CH | Br |
| CH₃ | Cl | Me | OCH₂CF₃ | CH | Br |
| CH₃ | Cl | Et | OCH₂CF₃ | CH | Br |
| CH₃ | Cl | i-Pr | OCH₂CF₃ | CH | Br |
| CH₃ | Cl | t-Bu | OCH₂CF₃ | CH | Br |
| CH₃ | Cl | H | OCHF₂ | CH | F |
| CH₃ | Cl | Me | OCHF₂ | CH | F |
| CH₃ | Cl | Et | OCHF₂ | CH | F |
| CH₃ | Cl | i-Pr | OCHF₂ | CH | F |
| CH₃ | Cl | t-Bu | OCHF₂ | CH | F |
| CH₃ | Cl | H | OCHF₂ | CH | Cl |
| CH₃ | Cl | Me | OCHF₂ | CH | Cl |
| CH₃ | Cl | Et | OCHF₂ | CH | Cl |
| CH₃ | Cl | i-Pr | OCHF₂ | CH | Cl |
| CH₃ | Cl | t-Bu | OCHF₂ | CH | Cl |
| CH₃ | Cl | H | OCHF₂ | CH | Br |
| CH₃ | Cl | Me | OCHF₂ | CH | Br |
| CH₃ | Cl | Et | OCHF₂ | CH | Br |
| CH₃ | Cl | i-Pr | OCHF₂ | CH | Br |
| CH₃ | Cl | t-Bu | OCHF₂ | CH | Br |
| CH₃ | CN | H | CF₃ | N | F |
| CH₃ | CN | Me | CF₃ | N | F |
| CH₃ | CN | Et | CF₃ | N | F |
| CH₃ | CN | i-Pr | CF₃ | N | F |
| CH₃ | CN | t-Bu | CF₃ | N | F |
| CH₃ | CN | H | CF₃ | N | Cl |
| CH₃ | CN | Me | CF₃ | N | Cl |
| CH₃ | CN | Et | CF₃ | N | Cl |
| CH₃ | CN | i-Pr | CF₃ | N | Cl |
| CH₃ | CN | t-Bu | CF₃ | N | Cl |
| CH₃ | CN | H | CF₃ | N | Br |
| CH₃ | CN | Me | CF₃ | N | Br |
| CH₃ | CN | Et | CF₃ | N | Br |
| CH₃ | CN | t-Bu | CF₃ | N | Br |
| CH₃ | CN | H | Cl | N | F |
| CH₃ | CN | Me | Cl | N | F |
| CH₃ | CN | Et | Cl | N | F |
| CH₃ | CN | i-Pr | Cl | N | F |
| CH₃ | CN | t-Bu | Cl | N | F |
| CH₃ | CN | H | Cl | N | Cl |
| CH₃ | CN | Me | Cl | N | Cl |
| CH₃ | CN | Et | Cl | N | Cl |
| CH₃ | CN | i-Pr | Cl | N | Cl |
| CH₃ | CN | t-Bu | Cl | N | Cl |
| CH₃ | CN | H | Cl | N | Br |
| CH₃ | CN | Me | Cl | N | Br |
| CH₃ | CN | Et | Cl | N | Br |
| CH₃ | CN | i-Pr | Cl | N | Br |
| CH₃ | CN | t-Bu | Cl | N | Br |
| CH₃ | CN | H | Br | N | F |
| CH₃ | CN | Me | Br | N | F |
| CH₃ | CN | Et | Br | N | F |
| CH₃ | CN | i-Pr | Br | N | F |
| CH₃ | CN | t-Bu | Br | N | F |
| CH₃ | CN | H | Br | N | Cl |
| CH₃ | CN | Me | Br | N | Cl |
| CH₃ | CN | Et | Br | N | Cl |
| CH₃ | CN | i-Pr | Br | N | Cl |
| CH₃ | CN | t-Bu | Br | N | Cl |
| CH₃ | CN | H | Br | N | Br |
| CH₃ | CN | Me | Br | N | Br |
| CH₃ | CN | Et | Br | N | Br |
| CH₃ | CN | i-Pr | Br | N | Br |
| CH₃ | CN | t-Bu | Br | N | Br |
| CH₃ | CN | H | OCH₂CF₃ | N | F |
| CH₃ | CN | Me | OCH₂CF₃ | N | F |
| CH₃ | CN | Et | OCH₂CF₃ | N | F |
| CH₃ | CN | i-Pr | OCH₂CF₃ | N | F |
| CH₃ | CN | t-Bu | OCH₂CF₃ | N | F |
| CH₃ | CN | H | OCH₂CF₃ | N | Cl |
| CH₃ | CN | Me | OCH₂CF₃ | N | Cl |
| CH₃ | CN | Et | OCH₂CF₃ | N | Cl |
| CH₃ | CN | i-Pr | OCH₂CF₃ | N | Cl |
| CH₃ | CN | t-Bu | OCH₂CF₃ | N | Cl |
| CH₃ | CN | H | OCH₂CF₃ | N | Br |
| CH₃ | CN | Me | OCH₂CF₃ | N | Br |
| CH₃ | CN | Et | OCH₂CF₃ | N | Br |
| CH₃ | CN | i-Pr | OCH₂CF₃ | N | Br |
| CH₃ | CN | t-Bu | OCH₂CF₃ | N | Br |
| CH₃ | CN | H | OCHF₂ | N | F |
| CH₃ | CN | Me | OCHF₂ | N | F |
| CH₃ | CN | Et | OCHF₂ | N | F |
| CH₃ | CN | i-Pr | OCHF₂ | N | F |
| CH₃ | CN | t-Bu | OCHF₂ | N | F |
| CH₃ | CN | H | OCHF₂ | N | Cl |
| CH₃ | CN | Me | OCHF₂ | N | Cl |
| CH₃ | CN | Et | OCHF₂ | N | Cl |
| CH₃ | CN | i-Pr | OCHF₂ | N | Cl |
| CH₃ | CN | t-Bu | OCHF₂ | N | Cl |
| CH₃ | CN | H | OCHF₂ | N | Br |
| CH₃ | CN | Me | OCHF₂ | N | Br |
| CH₃ | CN | Et | OCHF₂ | N | Br |
| CH₃ | CN | i-Pr | OCHF₂ | N | Br |
| CH₃ | CN | t-Bu | OCHF₂ | N | Br |
| CH₃ | CN | H | CF₃ | CH | F |
| CH₃ | CN | Me | CF₃ | CH | F |
| CH₃ | CN | Et | CF₃ | CH | F |
| CH₃ | CN | i-Pr | CF₃ | CH | F |
| CH₃ | CN | t-Bu | CF₃ | CH | F |
| CH₃ | CN | H | CF₃ | CH | Cl |
| CH₃ | CN | Me | CF₃ | CH | Cl |
| CH₃ | CN | Et | CF₃ | CH | Cl |
| CH₃ | CN | i-Pr | CF₃ | CH | Cl |
| CH₃ | CN | t-Bu | CF₃ | CH | Cl |
| CH₃ | CN | H | CF₃ | CH | Br |
| CH₃ | CN | Me | CF₃ | CH | Br |
| CH₃ | CN | Et | CF₃ | CH | Br |
| CH₃ | CN | i-Pr | CF₃ | CH | Br |
| CH₃ | CN | t-Bu | CF₃ | CH | Br |
| CH₃ | CN | H | Cl | CH | F |
| CH₃ | CN | Me | Cl | CH | F |
| CH₃ | CN | Et | Cl | CH | F |
| CH₃ | CN | i-Pr | Cl | CH | F |
| CH₃ | CN | t-Bu | Cl | CH | F |
| CH₃ | CN | H | Cl | CH | Cl |
| CH₃ | CN | Me | Cl | CH | Cl |
| CH₃ | CN | Et | Cl | CH | Cl |
| CH₃ | CN | i-Pr | Cl | CH | Cl |
| CH₃ | CN | t-Bu | Cl | CH | Cl |
| CH₃ | CN | H | Cl | CH | Br |
| CH₃ | CN | Me | Cl | CH | Br |
| CH₃ | CN | Et | Cl | CH | Br |
| CH₃ | CN | i-Pr | Cl | CH | Br |
| CH₃ | CN | t-Bu | Cl | CH | Br |
| CH₃ | CN | H | Br | CH | F |

TABLE 2-continued

| | | | | | |
|---|---|---|---|---|---|
| CH₃ | CN | Me | Br | CH | F |
| CH₃ | CN | Et | Br | CH | F |
| CH₃ | CN | i-Pr | Br | CH | F |
| CH₃ | CN | t-Bu | Br | CH | F |
| CH₃ | CN | H | Br | CH | Cl |
| CH₃ | CN | Me | Br | CH | Cl |
| CH₃ | CN | Et | Br | CH | Cl |
| CH₃ | CN | i-Pr | Br | CH | Cl |
| CH₃ | CN | t-Bu | Br | CH | Cl |
| CH₃ | CN | H | Br | CH | Br |
| CH₃ | CN | Me | Br | CH | Br |
| CH₃ | CN | Et | Br | CH | Br |
| CH₃ | CN | i-Pr | Br | CH | Br |
| CH₃ | CN | t-Bu | Br | CH | Br |
| CH₃ | CN | H | OCH₂CF | CH | F |
| CH₃ | CN | Me | OCH₂CF₃ | CH | F |
| CH₃ | CN | Et | OCH₂CF₃ | CH | F |
| CH₃ | CN | i-Pr | OCH₂CF₃ | CH | F |
| CH₃ | CN | t-Bu | OCH₂CF₃ | CH | F |
| CH₃ | CN | H | OCH₂CF₃ | CH | Cl |
| CH₃ | CN | Me | OCH₂CF₃ | CH | Cl |
| CH₃ | CN | Et | OCH₂CF₃ | CH | Cl |
| CH₃ | CN | i-Pr | OCH₂CF₃ | CH | Cl |
| CH₃ | CN | t-Bu | OCH₂CF₃ | CH | Cl |
| CH₃ | CN | H | OCH₂CF₃ | CH | Br |
| CH₃ | CN | Me | OCH₂CF₃ | CH | Br |
| CH₃ | CN | Et | OCH₂CF₃ | CH | Br |
| CH₃ | CN | i-Pr | OCH₂CF₃ | CH | Br |
| CH₃ | CN | t-Bu | OCH₂CF₃ | CH | Br |
| CH₃ | CN | H | OCHF₂ | CH | F |
| CH₃ | CN | Me | OCHF₂ | CH | F |
| CH₃ | CN | Et | OCHF₂ | CH | F |
| CH₃ | CN | i-Pr | OCHF₂ | CH | F |
| CH₃ | CN | t-Bu | OCHF₂ | CH | F |
| CH₃ | CN | H | OCHF₂ | CH | Cl |
| CH₃ | CN | Me | OCHF₂ | CH | Cl |
| CH₃ | CN | Et | OCHF₂ | CH | Cl |
| CH₃ | CN | i-Pr | OCHF₂ | CH | Cl |
| CH₃ | CN | t-Bu | OCHF₂ | CH | Cl |
| CH₃ | CN | H | OCHF₂ | CH | Br |
| CH₃ | CN | Me | OCHF₂ | CH | Br |
| CH₃ | CN | Et | OCHF₂ | CH | Br |
| CH₃ | CN | i-Pr | OCHF₂ | CH | Br |
| CH₃ | CN | t-Bu | OCHF₂ | CH | Br |

What is claimed is:

1. A method for preparing a compound of Formula 1

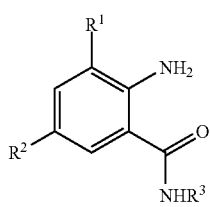

wherein
$R^1$ is $C_1$-$C_4$ alkyl, $C_1$-$C_4$ haloalkyl, $C_1$-$C_4$ alkoxy or $C_1$-$C_6$ haloalkoxy;
$R^2$ is F, Cl or cyano; and
$R^3$ is H, $C_1$-$C_4$ alkyl, $C_3$-$C_6$ cycloalkyl, $C_4$-$C_7$ cycloalkylalkyl, $C_4$-$C_7$ alkylcycloalkyl or cyclopropylcyclopropyl;
comprising contacting a compound of Formula 2

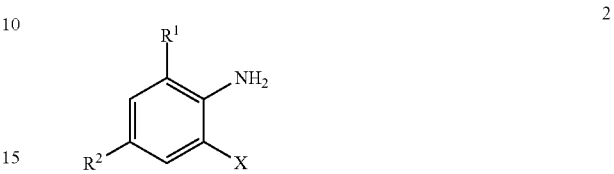

wherein
$R^1$ is $C_1$-$C_4$ alkyl, $C_1$-$C_4$ haloalkyl, $C_1$-$C_4$ alkoxy or $C_1$-$C_6$ haloalkoxy;
$R^2$ is F, Cl or cyano; and
X is Br or I;
with a compound of Formula 3

$$R^3NH_2 \qquad 3$$

wherein
$R^3$ is H, $C_1$-$C_4$ alkyl, $C_3$-$C_6$ cycloalkyl, $C_4$-$C_7$ cycloalkylalkyl, $C_4$-$C_7$ alkylcycloalkyl or cyclopropylcyclopropyl;
in the presence of a palladium source, a ligand, a base and carbon monoxide.

2. The method of claim 1 wherein $R^1$ is $C_1$-$C_4$ alkyl; and $R^2$ is Cl or cyano.

3. The method of claim 2 wherein $R^1$ is methyl; and $R^2$ is chloro.

4. The method of claim 2 wherein $R^1$ is methyl; and $R^2$ is cyano.

5. The method of claim 1 wherein X is Br.

6. The method of claim 1 wherein $R^3$ is H, methyl, isopropyl or cyclopropylcyclopropyl.

7. The method of claim 1 wherein $R^1$ is methyl; $R^2$ is Cl or cyano; and $R^3$ is methyl.

8. The method of claim 1 wherein the base is an organic base comprising a compound of Formula 3; $R^3$ is methyl or isopropyl; and the base is in a mole ratio of at least about 2 relative to a compound of Formula 2.

9. The method of claim 1 wherein the palladium source is a palladium(II) species and the ligand is selected from 1,1'-bis(diphenylphosphino)ferrocene and 1,4-bis(diphenylphosphino)butane.

10. The method of claim 9 wherein the palladium source is palladium(II) acetate and the ligand is 1,4-bis(diphenylphosphino)butane.

11. The method of claim 1 wherein the contacting is performed in a suitable solvent comprising ethylene glycol and N,N-dimethylethanolamine.

* * * * *